(12) United States Patent
Wu et al.

(10) Patent No.: US 10,040,813 B2
(45) Date of Patent: Aug. 7, 2018

(54) COMPOUNDS AS POSITIVE ALLOSTERIC MODULATORS FOR ERYTHROPOIETIN AND ERYTHROPOIETIN RECEPTOR TO TREAT ERYTHROPOIETIN DEFICIENCY DISEASES

(71) Applicant: Rong-Tsun Wu, Taipei (TW)

(72) Inventors: Rong-Tsun Wu, Taipei (TW); Lin-Yea Horng, Taipei (TW)

(73) Assignee: ACAHEALTH PHARMA & BIOTECH CO., LTD., New Taipei (TW)

(*) Notice: Subject to any disclaimer, the term of this patent is extended or adjusted under 35 U.S.C. 154(b) by 23 days.

(21) Appl. No.: 15/218,784

(22) Filed: Jul. 25, 2016

(65) Prior Publication Data
US 2017/0027970 A1 Feb. 2, 2017

Related U.S. Application Data

(60) Provisional application No. 62/195,916, filed on Jul. 23, 2015.

(51) Int. Cl.
*C07H 15/203* (2006.01)
*C07H 15/20* (2006.01)

(52) U.S. Cl.
CPC ............ *C07H 15/203* (2013.01); *C07H 15/20* (2013.01)

(58) Field of Classification Search
CPC .............................. C07H 15/203; C07H 15/20
See application file for complete search history.

(56) References Cited

U.S. PATENT DOCUMENTS

| | | | |
|---|---|---|---|
| 8,980,954 B2* | 3/2015 | Vander Jagt | A61K 31/381 514/733 |
| 2010/0160243 A1* | 6/2010 | Wu | A61K 31/7034 514/23 |

* cited by examiner

*Primary Examiner* — Jonathan S Lau
(74) *Attorney, Agent, or Firm* — WPAT, PC

(57) ABSTRACT

Disclosed are compounds which can act as a positive allosteric modulator for erythropoietin and erythropoietin receptor and have the activity in promoting erythropoiesis. Also disclosed are pharmaceutical compositions comprising said compounds and treatment methods utilizing said compounds.

15 Claims, 6 Drawing Sheets

* p<0.05 ,  p<0.01, * p<0.001

COMPOUNDS AS POSITIVE ALLOSTERIC MODULATORS FOR ERYTHROPOIETIN AND ERYTHROPOIETIN RECEPTOR TO TREAT ERYTHROPOIETIN DEFICIENCY DISEASES

FIELD OF THE INVENTION

The present invention relates to new compounds as positive allosteric modulators for erythropoietin and erythropoietin receptor to treat erythropoietin deficiency diseases, as well as pharmaceutical compositions and treatment methods thereof.

BACKGROUND OF THE INVENTION

Erythropoietin (EPO) is a glycoprotein hormone mainly produced in adult kidney and fetal liver. EPO exerts its effect by binding to erythropoietin receptor (EPO receptor) on cell surface. When cells sense a relatively low oxygen level (such as the hypoxia), EPO will be produced and released to regulate the proliferation, differentiation, maturation, and survival in erythroid lineage cells. Abnormal EPO levels in the blood stream could be the indicator for bone marrow and renal diseases. Relatively lower EPO levels are seen in patients with CKD, primary polycythemia rubra vera and chemotherapy-induced anemia.

Besides to be produced in kidney and liver, the expressions of EPO and EPO receptor are also found in non-erythroid tissues and organs, including brain, eye, heart, lung, gut, pancreas, muscle, uterus and gonads. Endogenous EPO-EPO receptor signaling contributes to wound healing responses, angiogenesis and local tissue-protective functions, such as neuroprotection, cardiovascular protection and protection from tissue ischemia and ischemia/reperfusion injury. It is reported that EPO treatment has renoprotective effects by reducing the extent of renal dysfunction and facilitating the recovery from cisplatin-induced acute renal failure.

Erythropoiesis-stimulating agents (ESAs) are recommended by the National Kidney Foundation Kidney Disease Outcomes Quality Initiative guidelines to treat anemia of CKD in patients with treatment-responsive anemia. Recombinant human EPO (rHuEpo) is approved for use in anemia of CKD, anemia in cancer patients receiving chemotherapy, to reduce transfusion requirements in surgical patients and to treat anemia in zidovudine-treated patients infected with the human immunodeficiency virus. A novel erythropoiesis stimulating protein (NESP), designed from EPO with longer plasma half-life, has been approved for the treatment of anemia by chronic renal failure. It is recommended that intravenous (i.v.) or subcutaneous (s.c.) administration should be more than once per week for maintenance therapy. However, the pain, the inconvenience for frequent injection and the development of anti-Epo antibodies due to the inherent antigenicity of rHuEpo should all be concerned. Furthermore, ESAs have safety risks in patients with higher hemoglobin levels and have complications such as hypertension, thromboembolism, iron deficiency and severe pure red-cell aplasia. Accordingly, an improvement in stimulating erythropoiesis and/or enhancing kidney functions is desired.

EPO is essential for the regulation of the mass of erythrocytes in response to changes in tissue oxygenation during hypoxia and anemia. The protective effects of EPO have been demonstrated in various tissues and experimental models of ischemia-induced injury and have been attributed to its effect on non-haematopoietic metabolic adaptation, inhibition of apoptosis and stimulation of angiogenesis. Recently, EPO has been reported to stimulate cardiac mitochondrial proliferation through the activation of mitochondrial biogenesis, which is mediated by PPAR co-activator 1-α (PGC-1α), a key regulator of cardiac bioenergetics. Clinically, EPO reverses cardiac remodeling, improves cardiac function, and enhances the exercise tolerance and quality of life of patients by inducing protective effects beyond the correction of anemia. These findings highlight the possibility that EPO-mediated protection may depend on its modulatory effects on intracellular energetics.

Hemoglobin (Hb) is the main oxygen transporter in erythrocytes. Its main form, Hb-α, is a tetramer consisting of two α- and β-polypeptide chains, each carrying a haeme group. Recently, Hb was unexpectedly found to be expressed in many non-haematopoietic cells and it is possible that it facilitates tissue oxygen transport or increases cellular oxygenation and so provides an intrinsic protective mechanism against hypoxic/ischemic injury.

EPO acts primarily to regulate erythropoiesis in the bone marrow by stimulating erythroid progenitor cell survival, proliferation and differentiation to produce mature red blood cells. EPO receptor expression on endothelial cells, the endometrium (lining) of the uterus, skeletal muscle myoblasts, the heart, and endothelial cells and neural cells in the retina and brain allows EPO to also act as a survival or mitogenic factor on these nonhaematopoietic cells, providing the potential for a response to EPO in multiple tissues. EPO has been used widely for the treatment of anemia associated with chronic kidney disease and cancer chemotherapy for nearly 30 years.

BRIEF SUMMARY OF THE INVENTION

In one aspect, the invention provides a compound having a formula selected from the group consisting of:

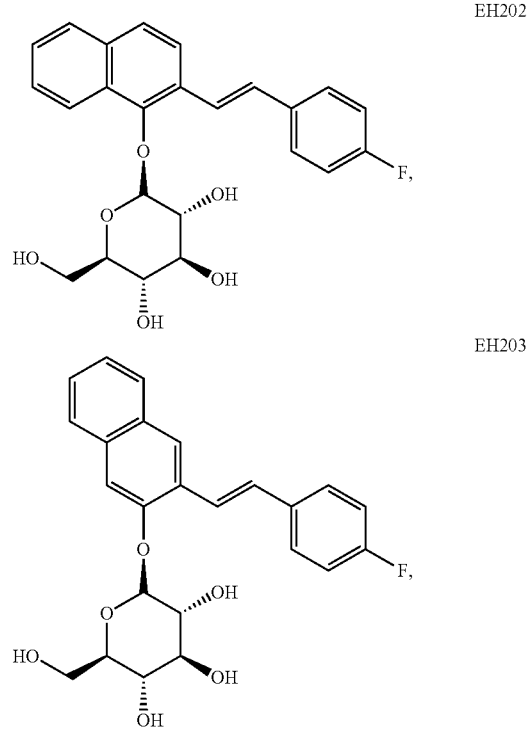

EH204
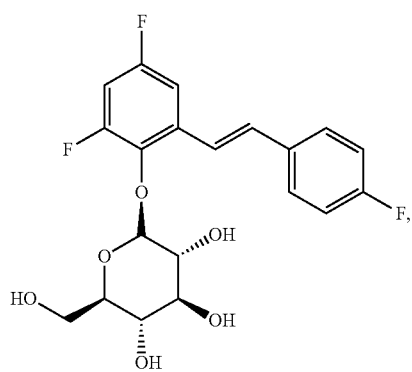
EH205
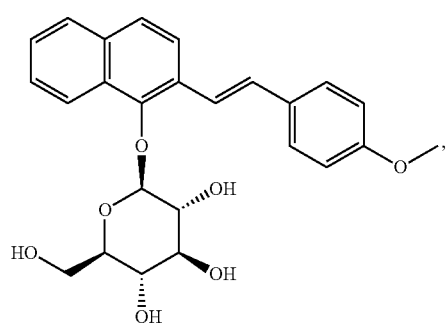
EH206
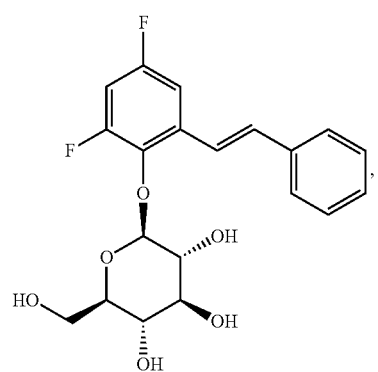
EH207
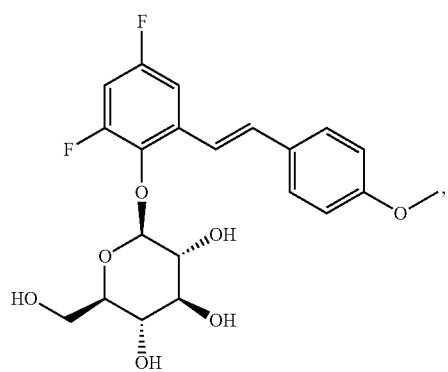
EH208
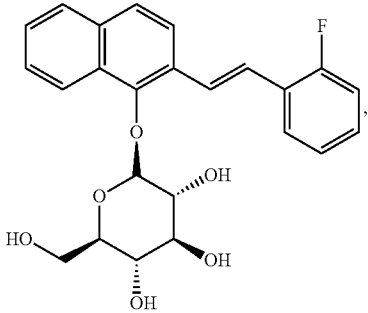
EH209
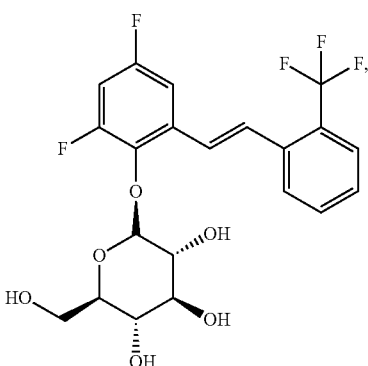
EH210
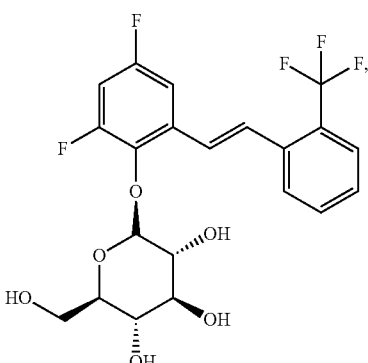
EH211
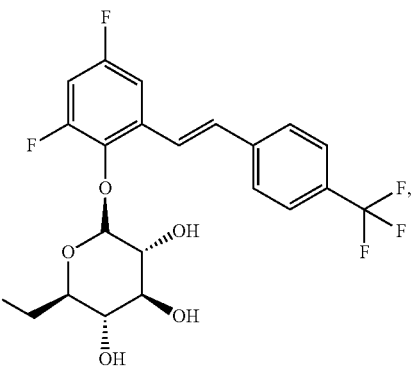

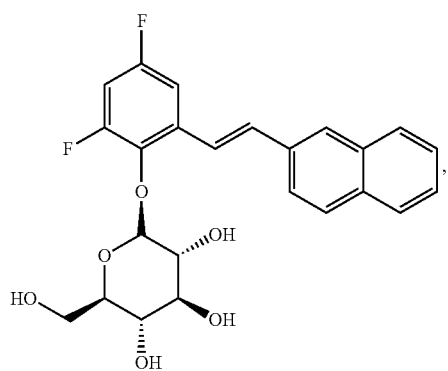
EH212
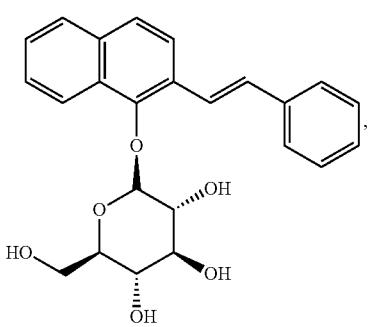
EH216
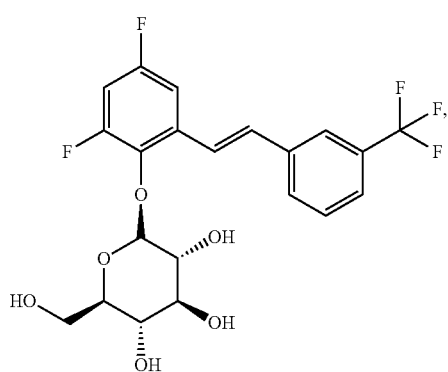
EH213
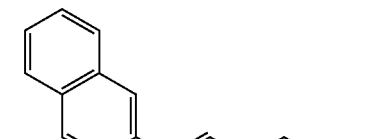
EH217
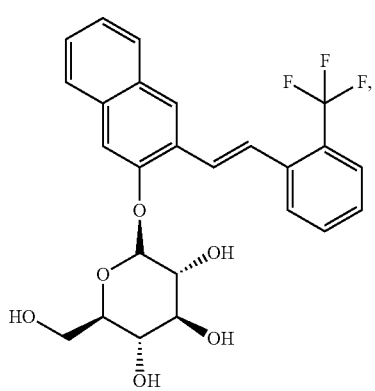
EH214
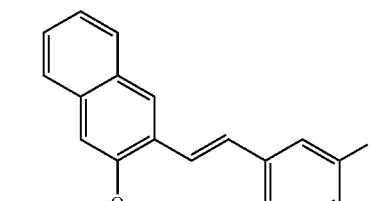
EH218
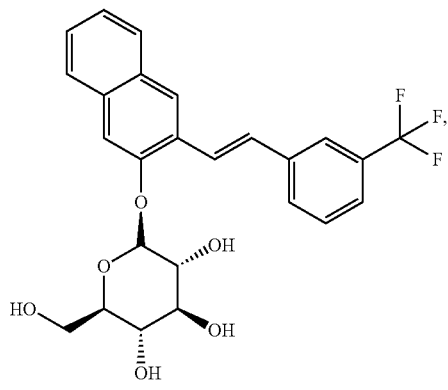
EH215
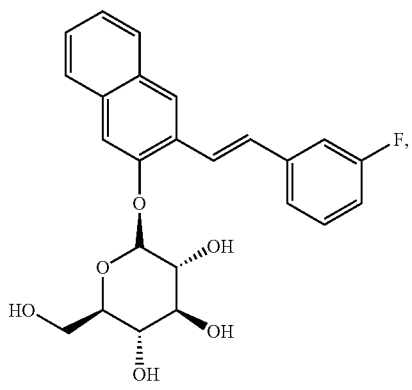
EH219

EH220
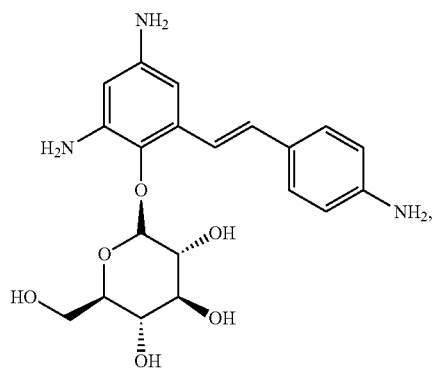
EH224
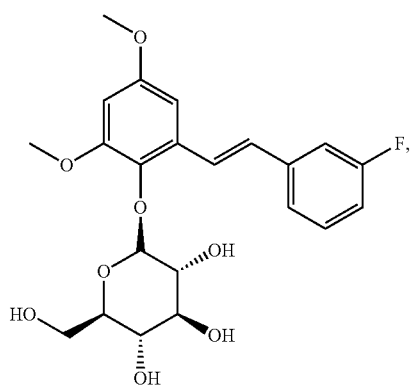
EH221
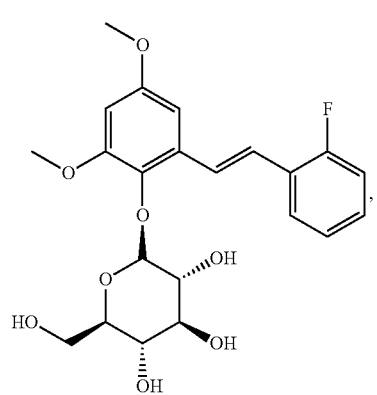
EH225
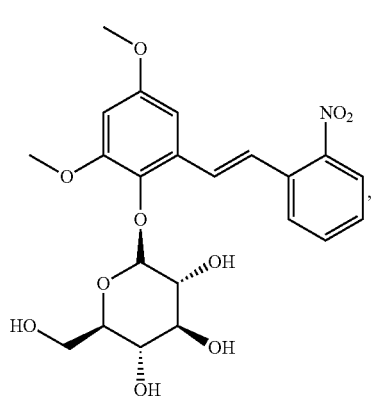
EH222
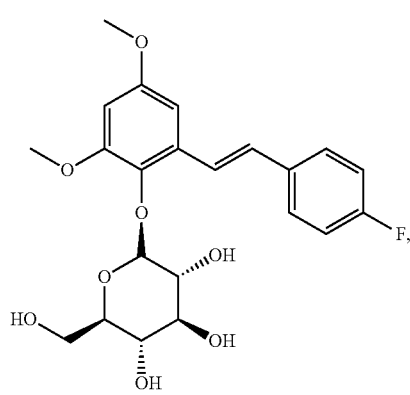
EH226
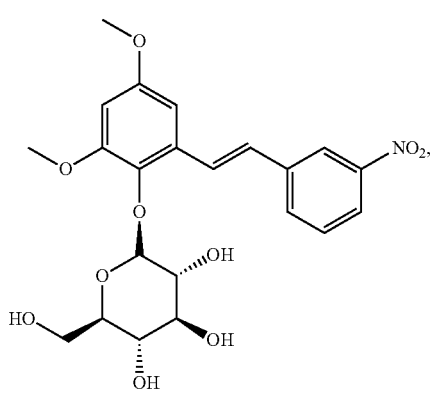
EH223
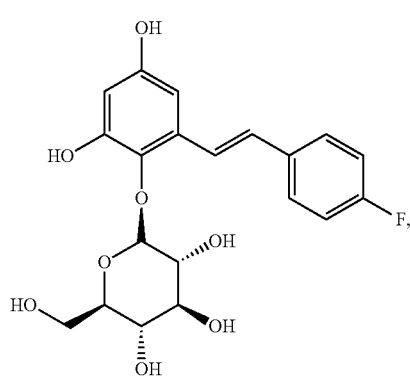
EH227
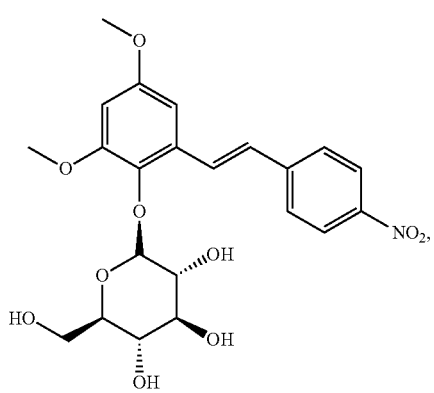

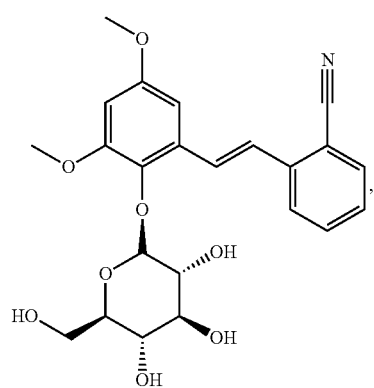
EH228
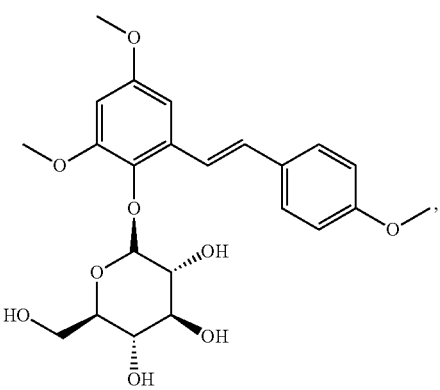
EH232
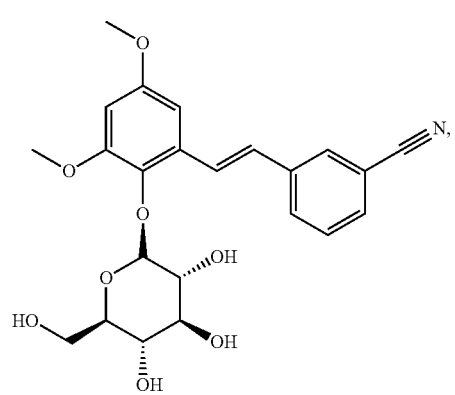
EH229
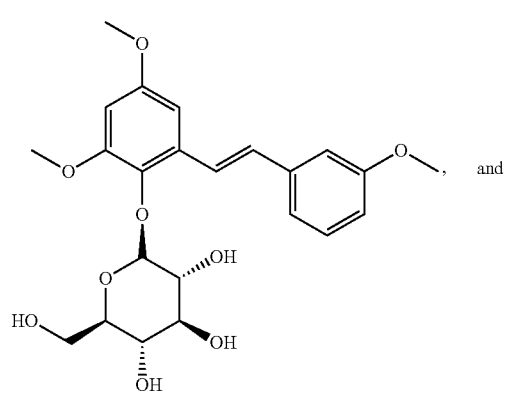
EH233
, and
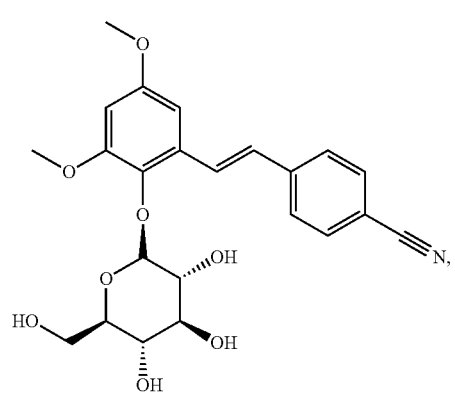
EH230
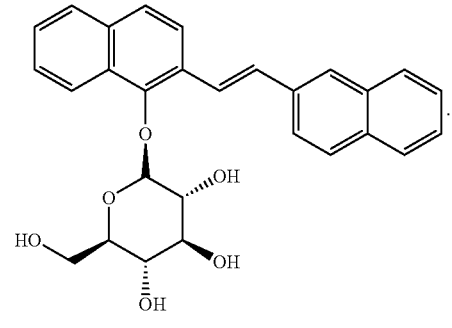
EH234
Preferably, the compound has a formula selected from the group consisting of:
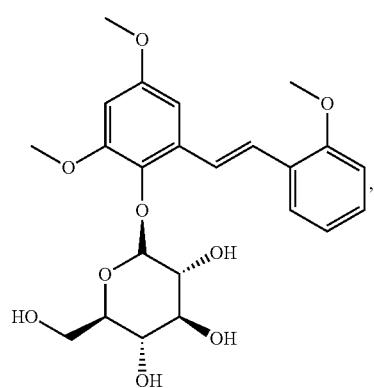
EH231
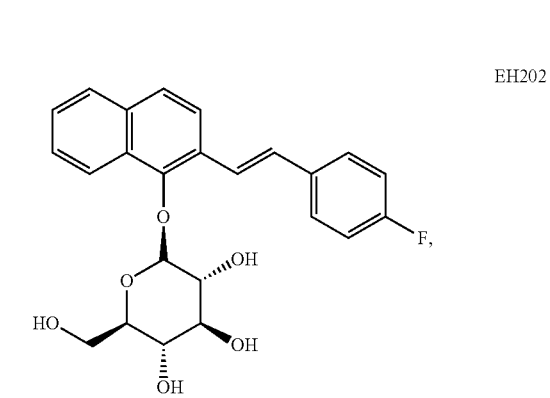
EH202

EH203

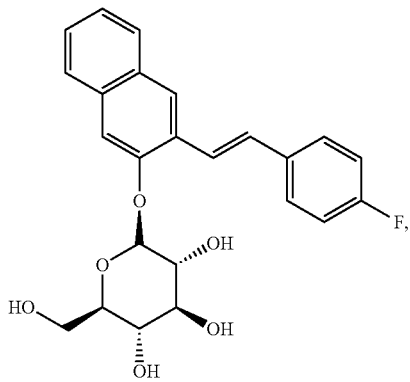

EH204

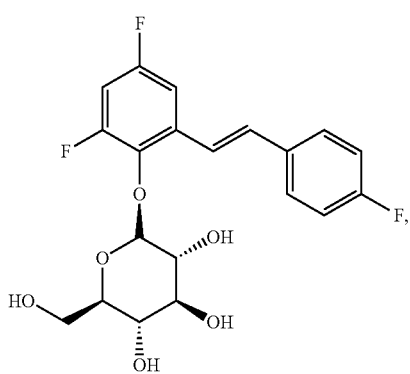

EH205

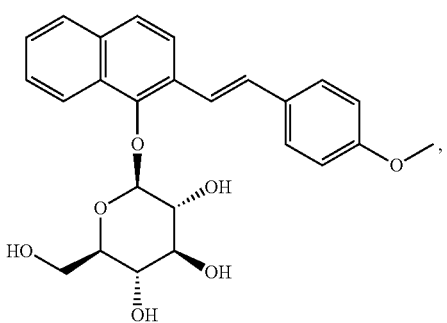

EH206

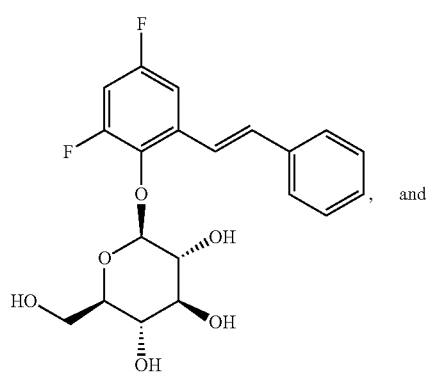, and

EH207

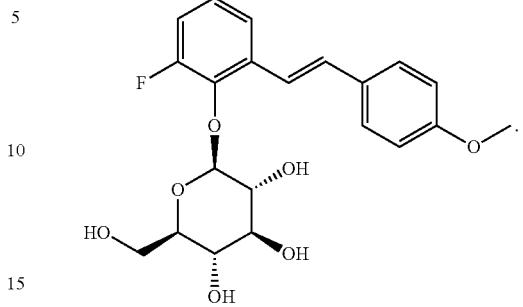

The compound of the present invention was found to be a positive allosteric modulator for erythropoietin and erythropoietin receptor, and may be used for treating an erythropoietin deficiency disease.

In another aspect, the present invention provides a pharmaceutical composition comprising a compound according to the present invention, and a pharmaceutically acceptable carrier.

The pharmaceutical composition of the present invention may be used to treat an erythropoietin deficiency disease.

In one further aspect, the present invention provides a method for treating an erythropoietin deficiency disease, comprising administering to a subject in need thereof an effective amount of a compound according to the present invention.

It is to be understood that both the foregoing general description and the following detailed description are exemplary and explanatory only and are not restrictive of the invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred.

In the drawings.

DETAILED DESCRIPTION OF THE INVENTION

Figure 1A:
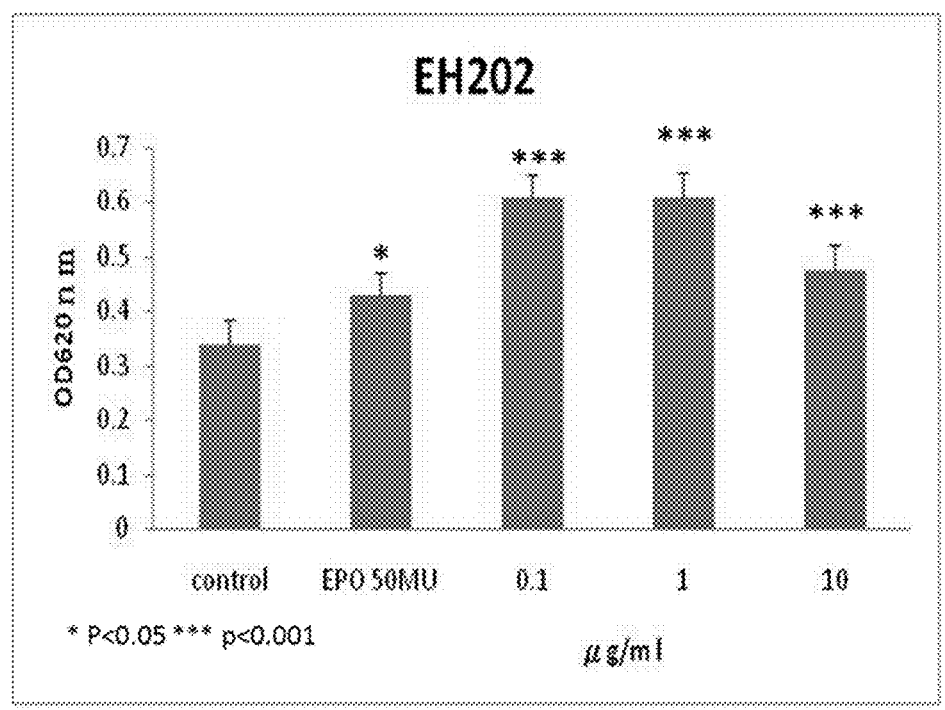
FIG. 1A shows the effect of EH202 on the formation of hemoglobin in bone marrow cells.
Figure 1B:
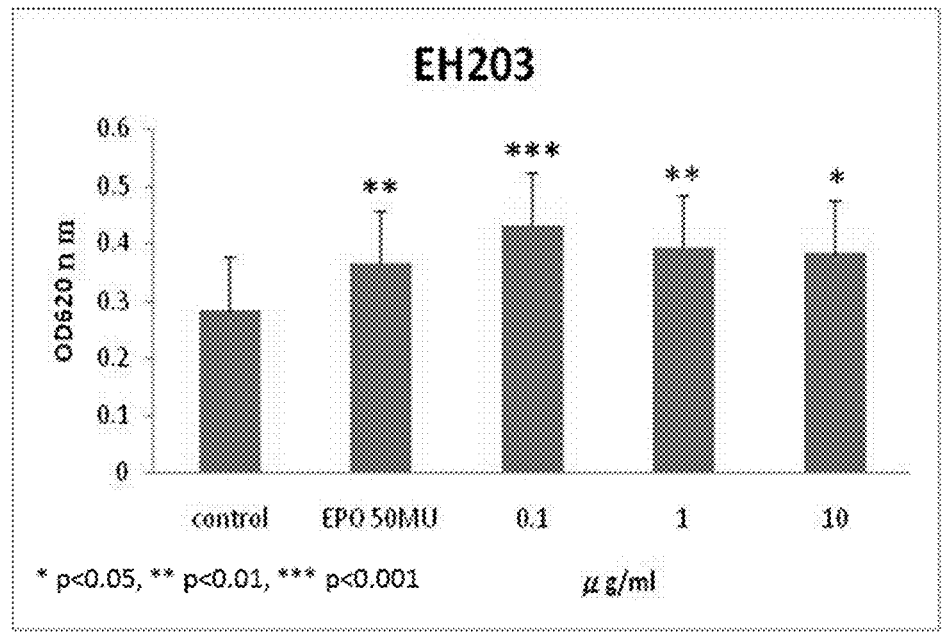
FIG. 1B shows the effect of EH203 on the formation of hemoglobin in bone marrow cells.
Figure 1C:
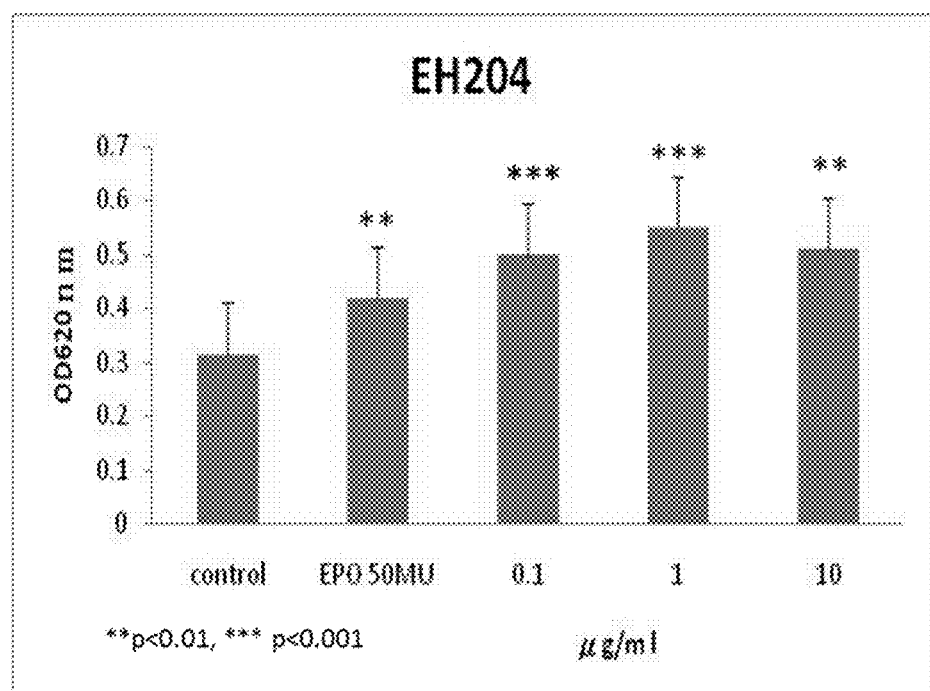
FIG. 1C shows the effect of EH204 on the formation of hemoglobin in bone marrow cells.
Figure 1D:
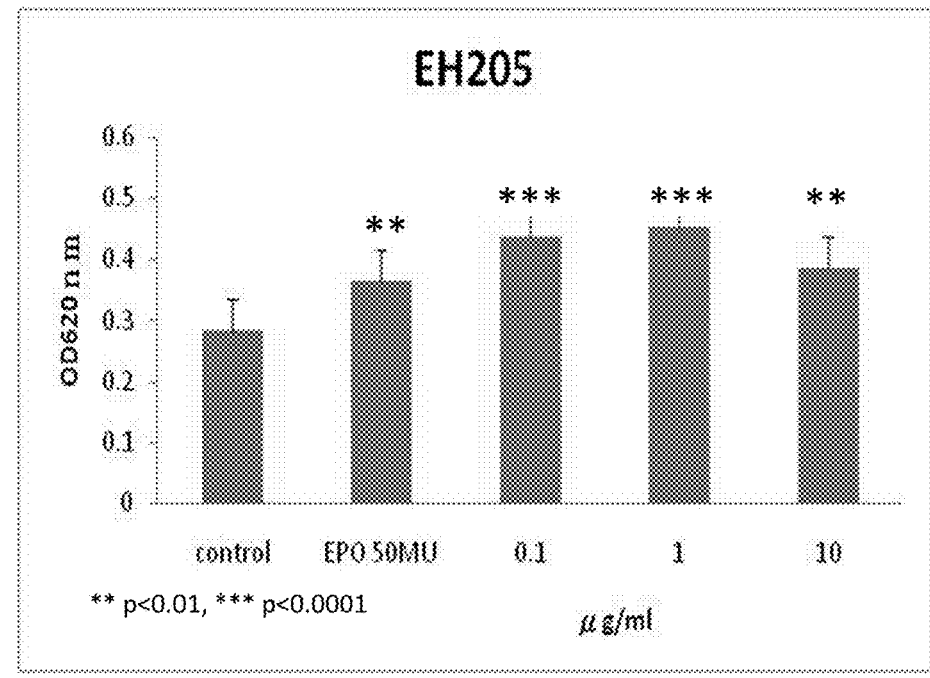
FIG. 1D shows the effect of EH205 on the formation of hemoglobin in bone marrow cells.
Figure 1E:
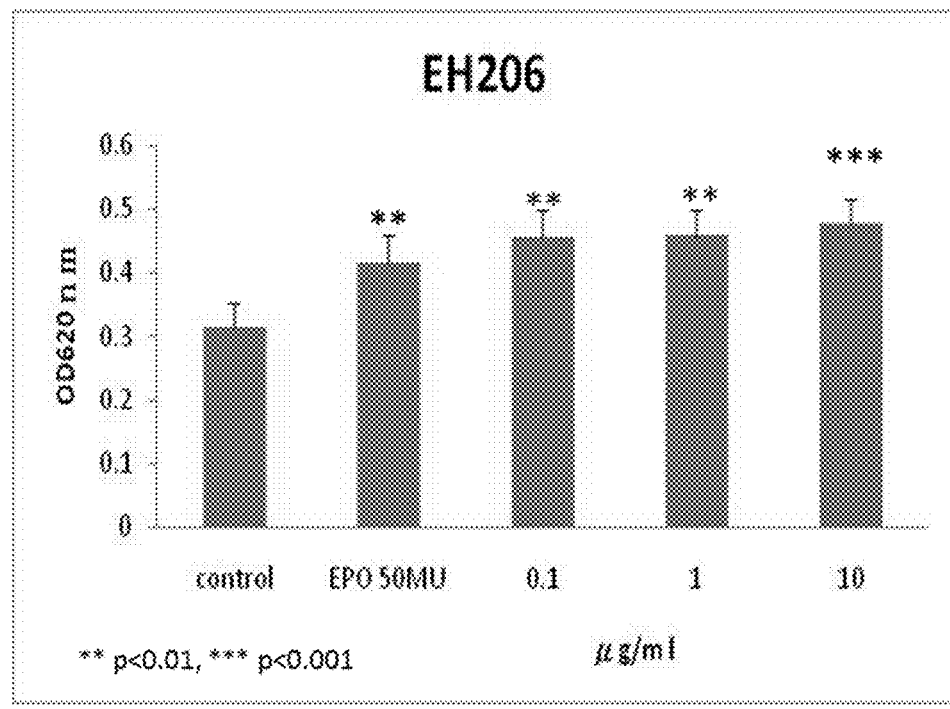
FIG. 1E shows the effect of EH206 on the formation of hemoglobin in bone marrow cells.
Figure 1F:
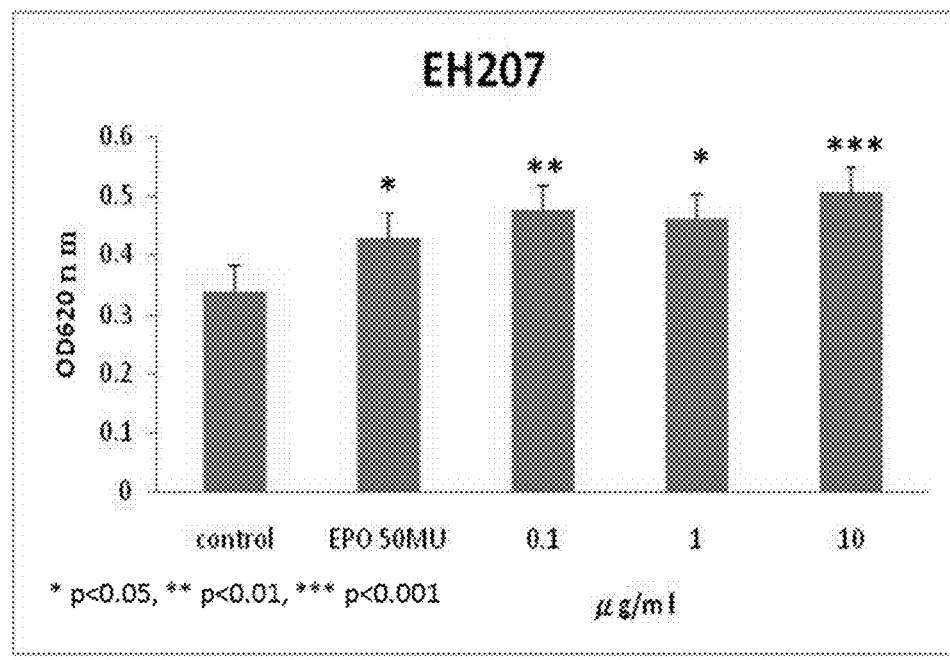
FIG. 1F shows the effect of EH207 on the formation of hemoglobin in bone marrow cells.
Figure 1G:
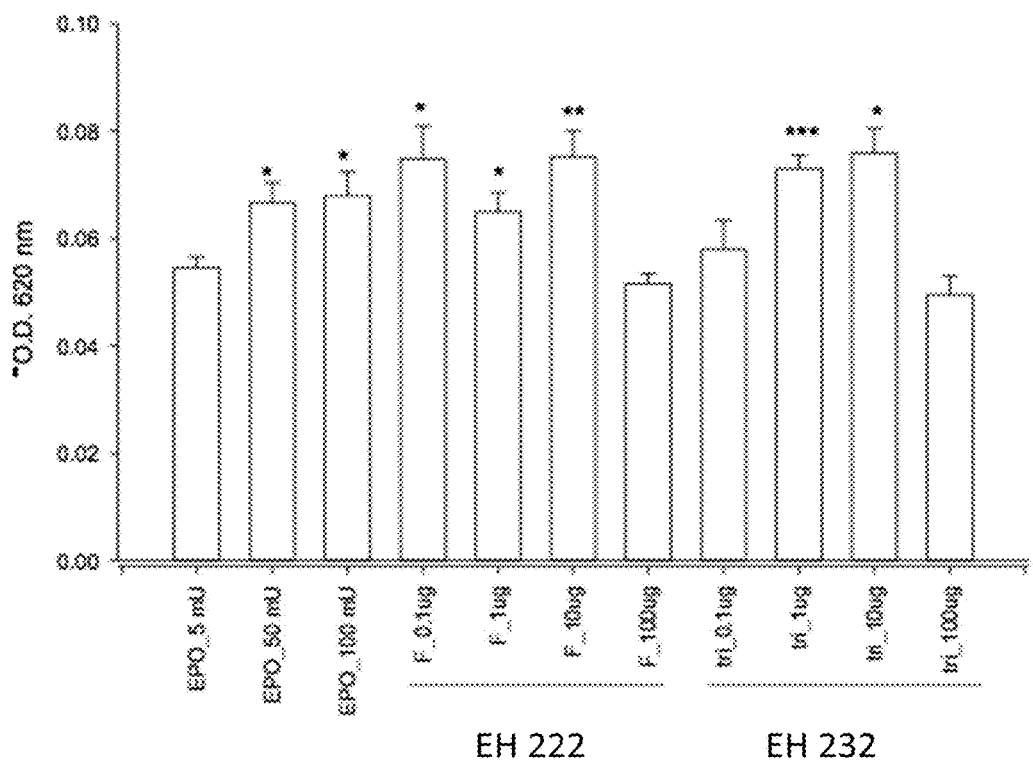
FIG. 1G shows the effect of EH222 and EH232 on the formation of hemoglobin in bone marrow cells.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximately, meaning that the term "around", "about" or "approximately" can be inferred if not expressly stated.

In one aspect, the invention provides a compound having a formula selected from the group consisting of:

EH202
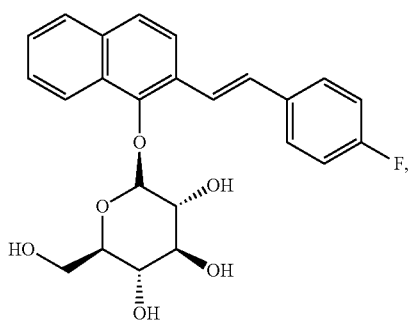

EH203
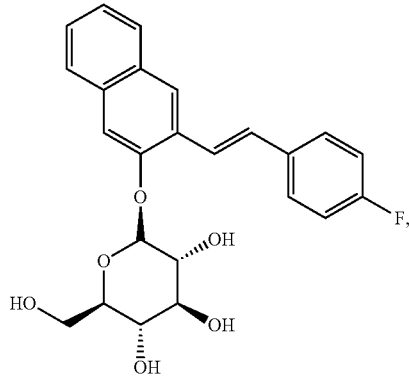

EH204
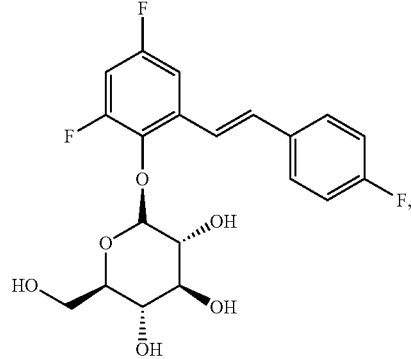

EH205
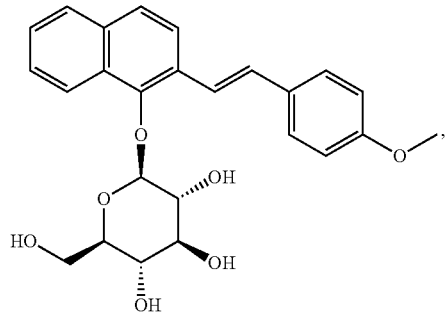

EH206
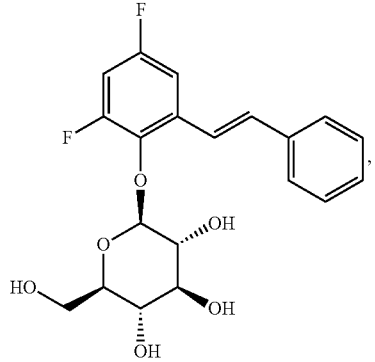

EH207
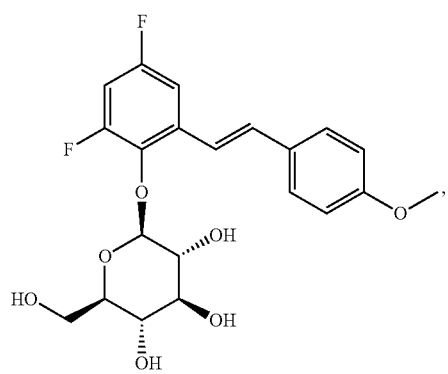
EH211
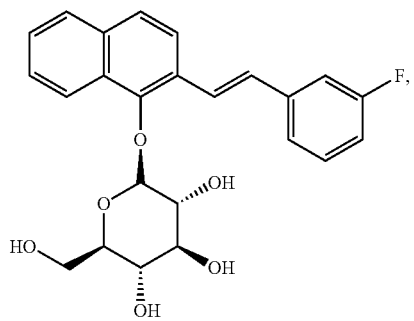
EH208
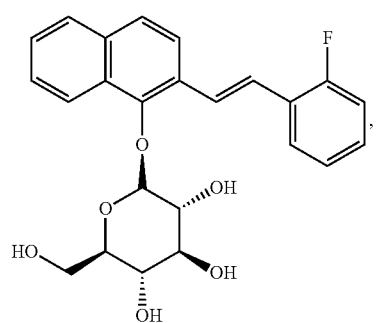
EH212
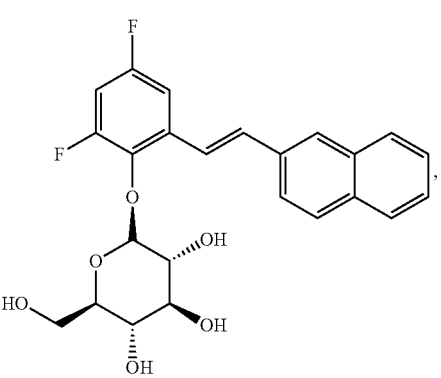
EH209
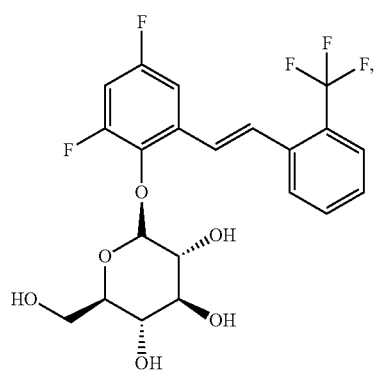
EH213
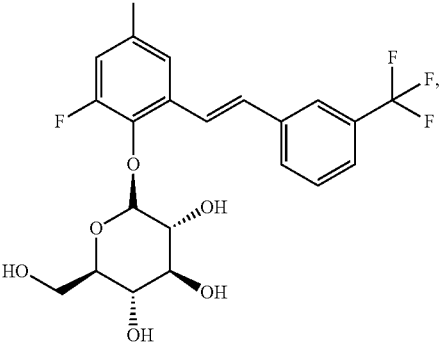
EH210
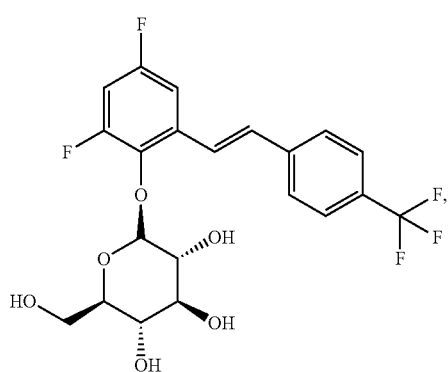
EH214
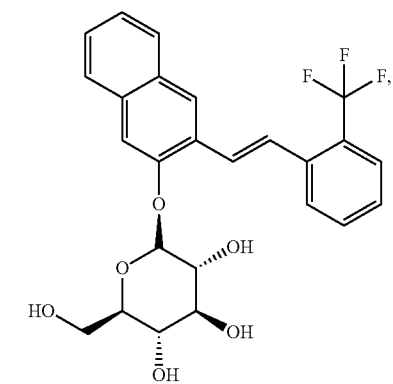

-continued
EH215
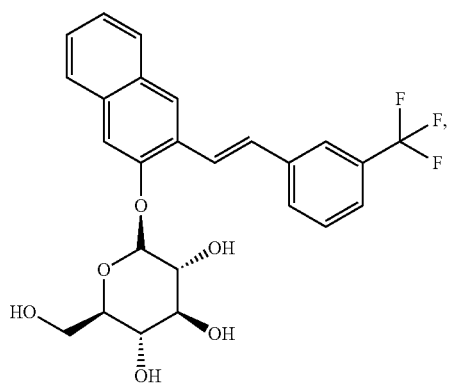
EH216
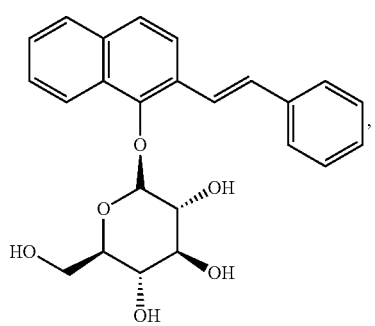
EH217
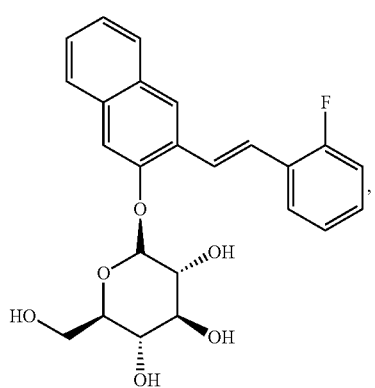
EH218
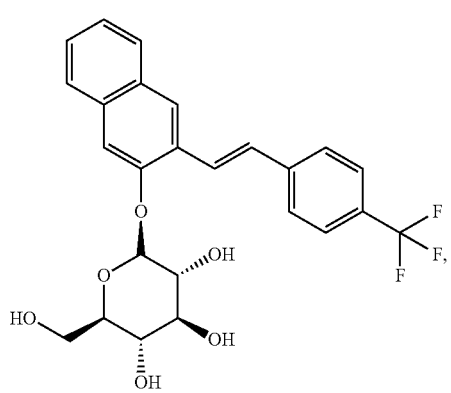
-continued
EH219
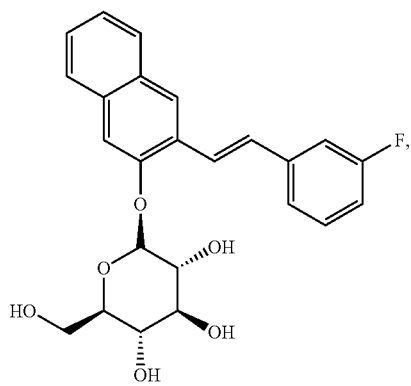
EH220
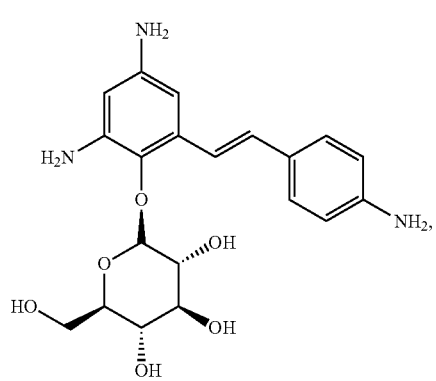
EH221
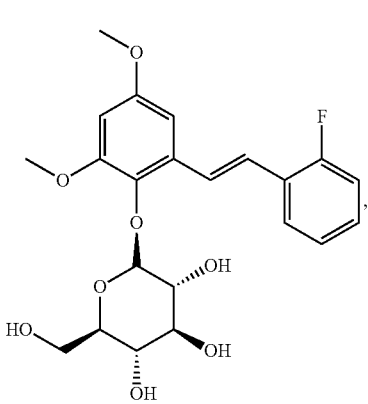
EH222
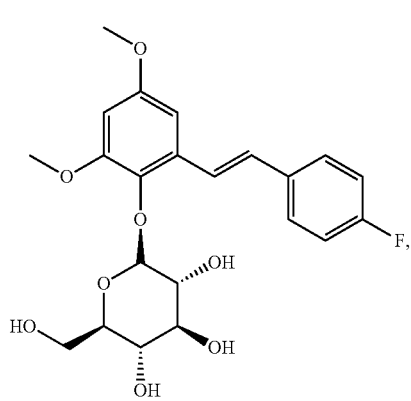

EH223
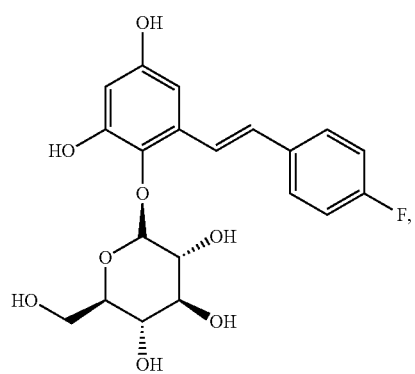
EH224
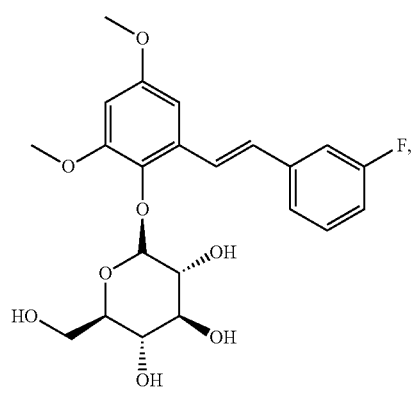
EH225
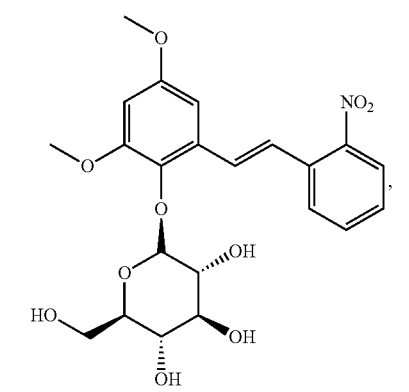
EH226
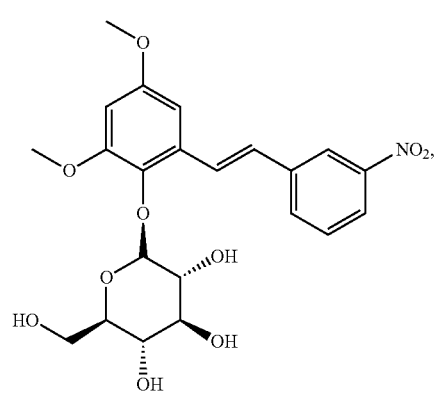
EH227
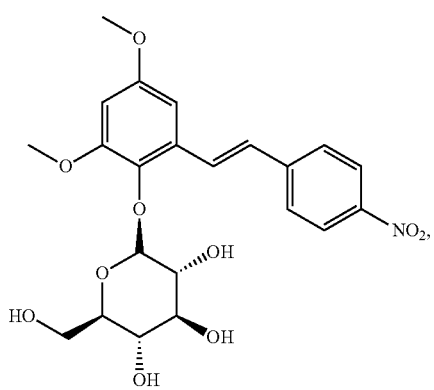
EH228
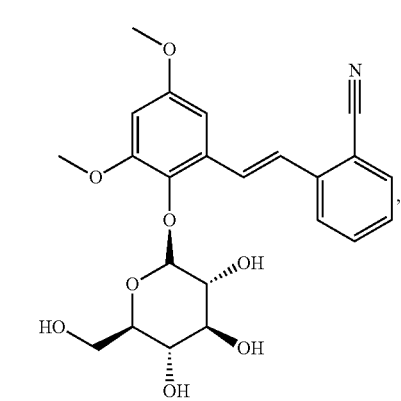
EH229
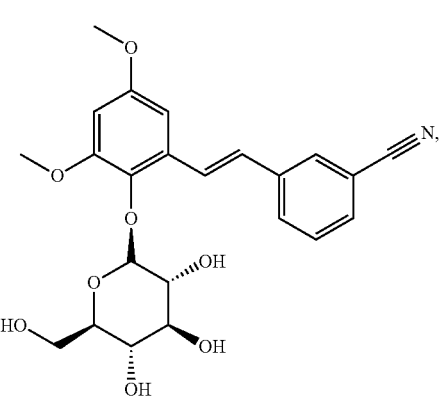
EH230
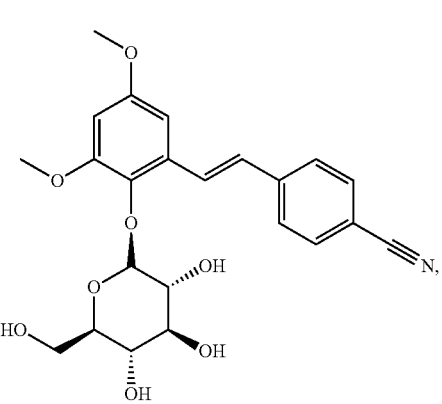

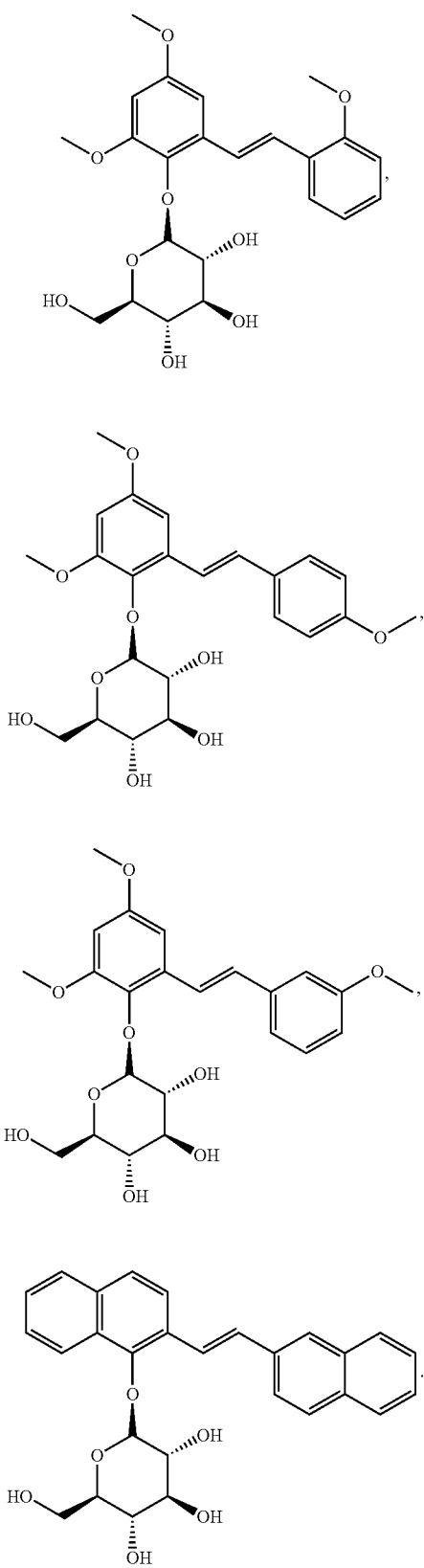

The chemical names of said compounds can be found in Table 1 below.

TABLE 1

Chemical name and structure of the compound

| Name | Structure |
|---|---|
| Formula (1), also called EH202: (Naphthanol-4'fluoro-stilbenzene)-1-O-β-D-glycoside | 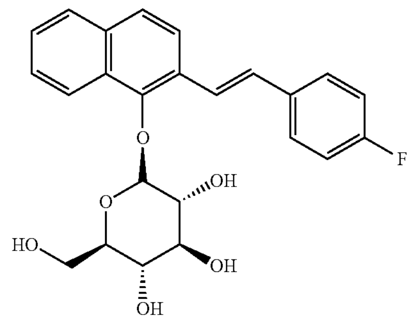 |
| Formula (2), also called EH203: (Naphthanol-4'-fluoro-stilbenzene)-2-O-β-D-glycoside | 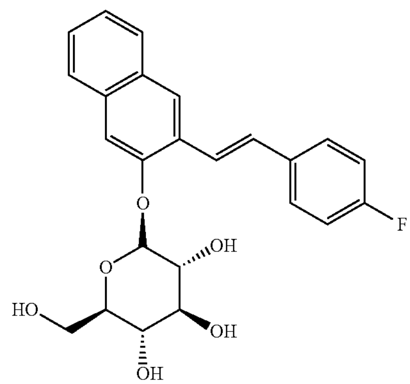 |
| Formula (3), also called EH204: (3,5,4'-trifluorophenol-stilbenzene)-2-O-β-D-glycoside | 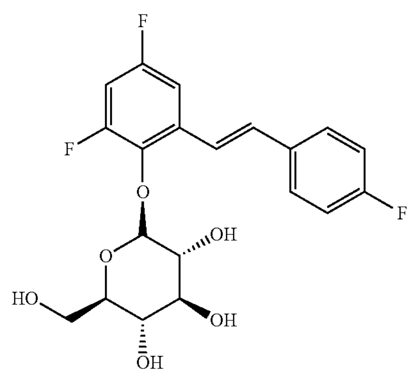 |
| Formula (4), also called EH205: (Naphthanol-4'-methoxy-stilbenzene)-1-O-β-D-glycoside | 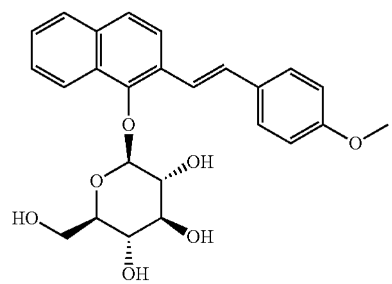 [SMILES: COc1ccc(/C=C/c2ccc3ccccc3c2O[C@@H]2O[C@H](CO)[C@@H](O)[C@H](O)[C@H]2O)cc1] |

TABLE 1-continued

Chemical name and structure of the compound

| Name | Structure |
|---|---|
| Formula (5), also called EH206: (3,5-difluoro-phenol-stilbenzene)-2-O-β-D-glycoside | 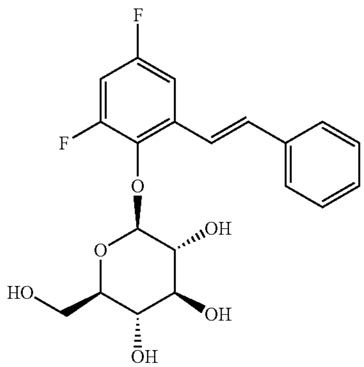 [SMILES: OC[C@H]1O[C@@H](Oc2c(F)cc(F)cc2/C=C/c2ccccc2)[C@H](O)[C@@H](O)[C@@H]1O] |
| Formula (6), also called EH207: (3,5-difluoro-phenol-4'-methoxy-stilbenzene)-2-O-β-D-glycoside | 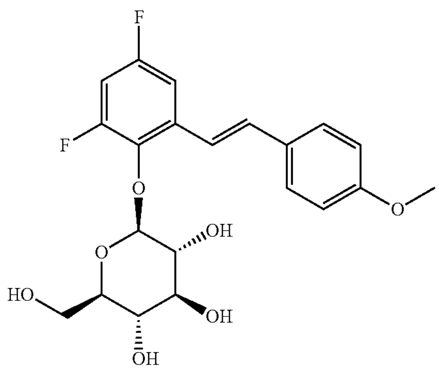 [SMILES: COc1ccc(/C=C/c2cc(F)cc(F)c2O[C@@H]2O[C@H](CO)[C@@H](O)[C@H](O)[C@H]2O)cc1] |
| Formula (7), also called EH208: (Naphthanol-2'-fluoro-stilbenzene)-1-O-β-D-glycoside | 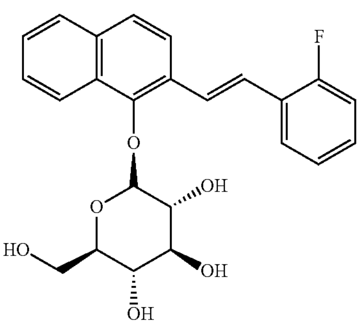 |
| Formula (8), also called EH209: (3,5-difluoro-phenol-2'-(trifluoromethyl)stilbenzene)-2-O-β-D-glycoside | 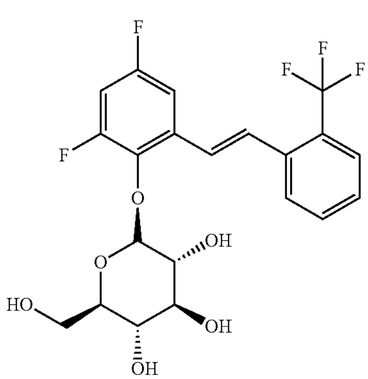 |
| Formula (9), also called EH210: (3,5-difluoro-phenol-4'-(trifluoromethyl)stilbenzene)-2-O-β-D-glycoside | |
| Formula (10), also called EH211: (Naphthanol-3'-methoxy-stilbenzene)-1-O-β-D-glycoside | |
| Formula (11), also called EH212: (Naphthanol-3',5'-difluoro-stilbenzene)-2'-O-β-D-glycoside | |
| Formula (12), also called EH213: (3,5-difluoro-phenol-3'-(trifluoromethyl)stilbenzene)-2-O-β-D-glycoside | |

TABLE 1-continued

Chemical name and structure of the compound

| Name | Structure |
|---|---|
| Formula (13), also called EH214: (Naphthanol-2'-(trifluoromethyl)stilbenzene)-2-O-β-D-glycoside | 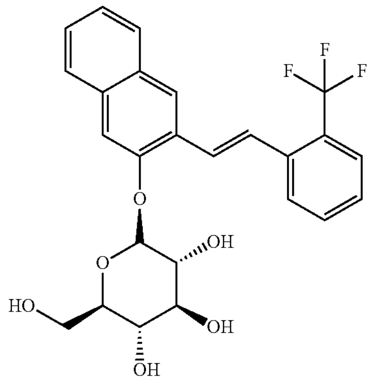 |
| Formula (14), also called EH215: (Naphthanol-3'-(trifluoromethyl)stilbenzene)-2-O-β-D-glycoside | 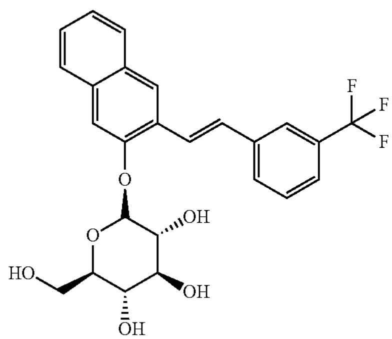 |
| Formula (15), also called EH216: (Naphthanol-stilbenzene)-1-O-β-D-glycoside | 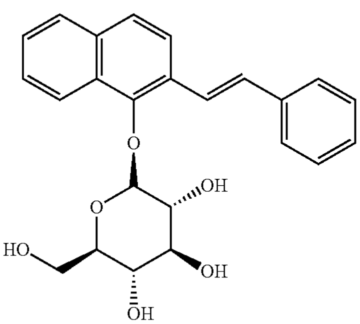 |
| Formula (16), also called EH217: (Naphthanol-2'-fluorostilbenzene)-2-O-β-D-glycoside | 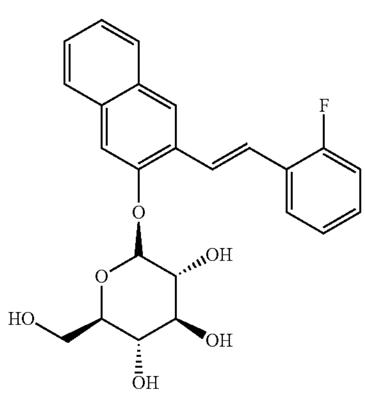 |
| Formula (17), also called EH218: (Naphthanol-4'-(trifluoromethyl)stilbenzene)-2-O-β-D-glycoside | |
| Formula (18), also called EH219: (Naphthanol-3'-fluorostilbenzene)-2-O-β-D-glycoside | |
| Formula (19), also called EH220: (3,5,4'-triamino-stilbenzene)-2-O-β-D-glycoside | |
| Formula (20), also called EH221: (3,5-dimethoxy-2'-fluoro-stilbenzene)-2-O-β-D-glycoside | |

TABLE 1-continued

Chemical name and structure of the compound

| Name | Structure |
|---|---|
| Formula (21), also called EH222: (3,5-dimethoxy-4'-fluoro-stilbenzene)-2-O-β-D-glycoside | 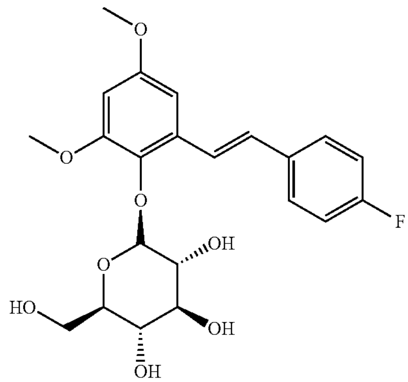 |
| Formula (22), also called EH223: (3,5-dihydroxy-4'-fluoro-stilbenzene)-2-O-β-D-glycoside | 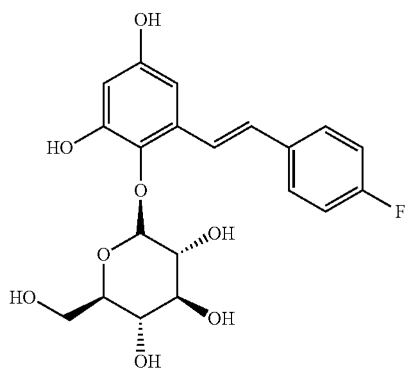 |
| Formula (23), also called EH224: (3,5-dimethoxy-3'-fluoro-stilbenzene)-2-O-β-D-glycoside | 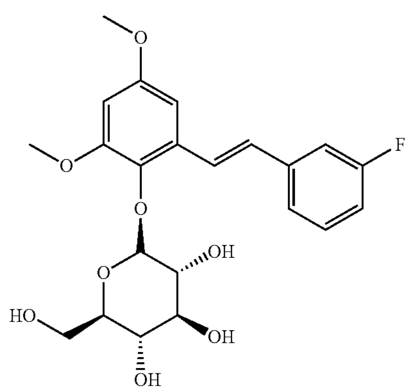 |
| Formula (24), also called EH225: (3,5-dimethoxy-2'-nitrostilbenzene)-2-O-β-D-glycoside | 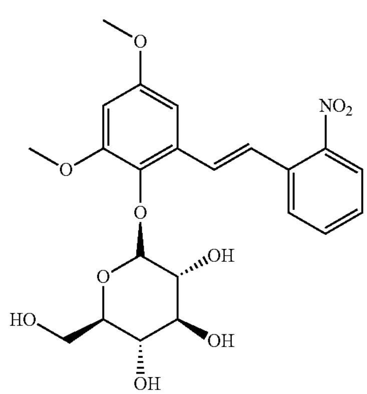 |
| Formula (25), also called EH226: (3,5-dimethoxy-3'-nitrostilbenzene)-2-O-β-D-glycoside | 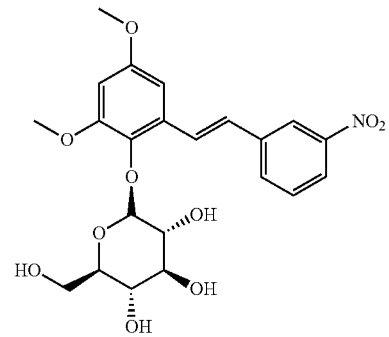 |
| Formula (26), also called EH227: (3,5-dimethoxy-4'-nitrostilbenzene)-2-O-β-D-glycoside | 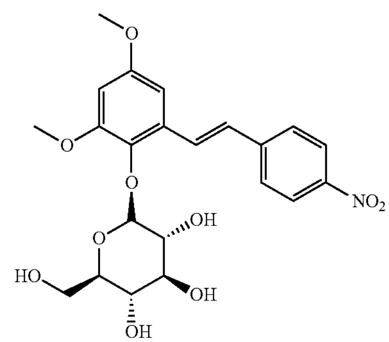 |
| Formula (27), also called EH228: (3,5-dimethoxy-2'-cyanostilbenzene)-2-O-β-D-glycoside | 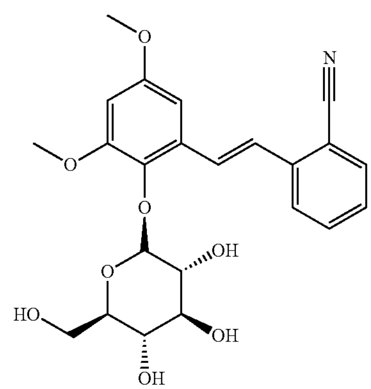 |
| Formula (28), also called EH229: (3,5-dimethoxy-3'-cyanostilbenzene)-2-O-β-D-glycoside | 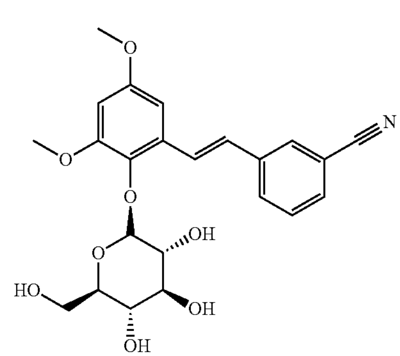 |

TABLE 1-continued

Chemical name and structure of the compound

| Name | Structure |
|---|---|
| Formula (29), also called EH230: (3,5-dimethoxy-4'-cyanostilbenzene)-2-O-β-D-glycoside | 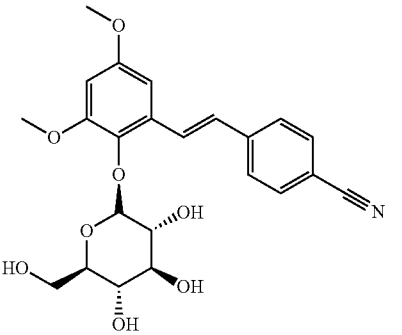 |
| Formula (30), also called EH231: (3,5,2'-trimethoxy-stilbenzene)-2-O-β-D-glycoside | 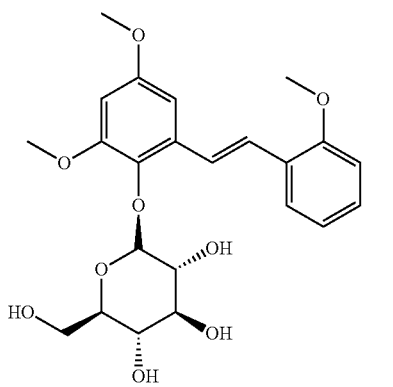 |
| Formula (31), also called EH232: (3,5,4'-trimethoxy-stilbenzene)-2-O-β-D-glycoside | 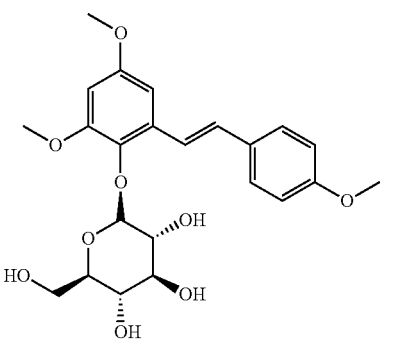 |
| Formula (32), also called EH233: (3,5,3'-trimethoxy-stilbenzene)-2-O-β-D-glycoside | 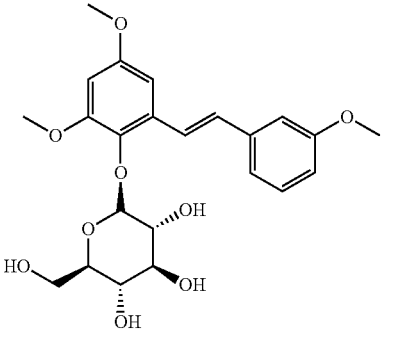 |
| Formula (33), also called EH234: (E)-2-(2-(naphthalen-2-yl)vinyl)naphthaol-1-O-β-D-glycoside | 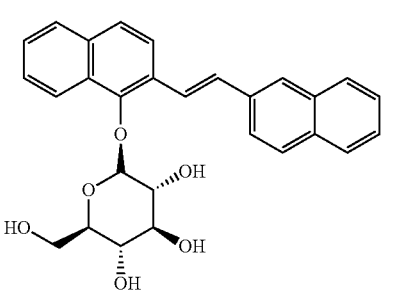 |

Preferably, the compound has a formula selected from the group consisting of:

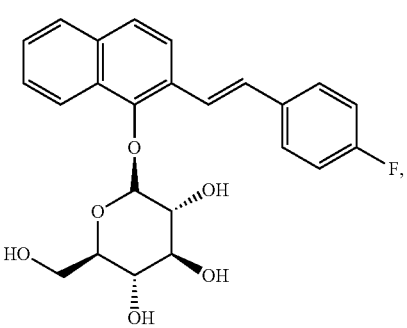

EH202

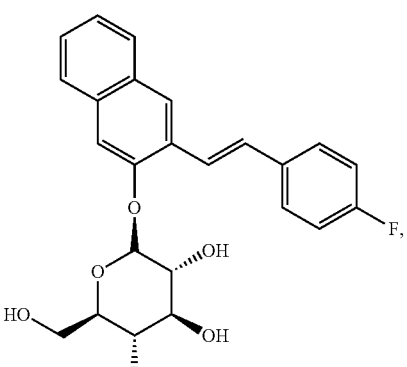

EH203

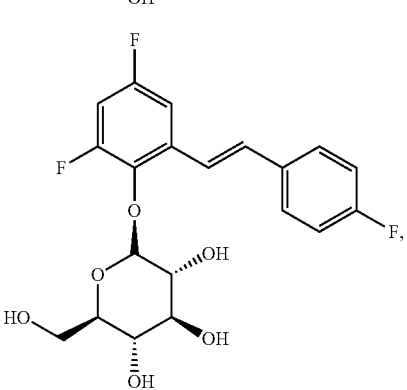

EH204

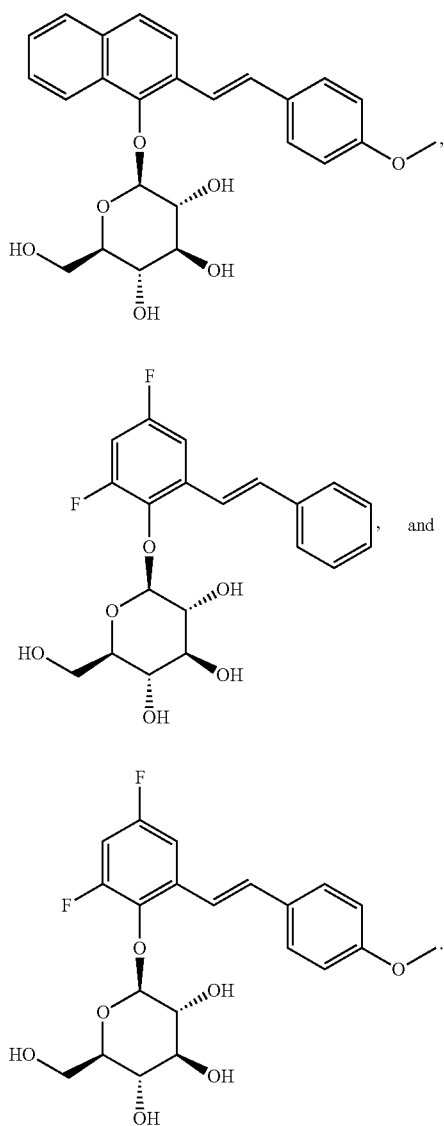

EH205

EH206

EH207

The compound of the present invention was found to be a positive allosteric modulator for erythropoietin and erythropoietin receptor and has the activity in promoting erythropoiesis. Accordingly, the compound of the present invention may be used in treating an erythropoietin deficiency disease.

A positive allosteric modulator (PAM) or allosteric enhancer induces an amplification of the orthosteric agonist's effect, either by enhancing the binding affinity or the functional efficacy of the orthosteric agonist for the target protein (May, L. T. et al., Annual review of pharmacology and toxicology 47, 1-51 (2007)).

The compound of the present invention may be chemically synthesized through a process known in the art.

In another aspect, the present invention provides a pharmaceutical composition comprising a compound according to the present invention, and a pharmaceutically acceptable carrier.

The pharmaceutical composition of the present invention may be used to treat an erythropoietin deficiency disease.

In one further aspect, the present invention provides a method for treating an erythropoietin deficiency disease. The method comprises administering to a subject in need thereof an effective amount of a compound according to the present invention.

According to the present invention, the erythropoietin deficiency disease includes but is not limited to anemia, a chronic kidney disease, chronic heart failure, a neurodegenerative disease, age-related macular degeneration, a chronic obstructive pulmonary disease, an anemic cancer in a patient undergoing chemotherapy, dry eye, and aging related insomnia.

In certain embodiments of the present invention, the erythropoietin deficiency disease is anemia associated with a kidney disease. The kidney disease includes but is not limited to a chronic kidney disease, an acute kidney injury, renal ischemia, renal failure, and a combination thereof.

Examples for a neurodegenerative disease include amyotrophic lateral sclerosis, Alzheimer's disease, Huntington's disease, and Parkinson's disease.

The pharmaceutical composition of the present invention can be manufactured by conventionally known methods with one or more pharmaceutically acceptable carriers. The term "pharmaceutically acceptable carrier" as used herein encompasses any of the standard pharmaceutical carriers. Such carriers may include, but are not limited to: saline, buffered saline, dextrose, water, glycerol, ethanol, propylene glycol, cremophor, nanoparticles, liposome, polymer, and combinations thereof.

The pharmaceutical composition of the present invention may be constituted into any form suitable for the mode of administration selected. For example, compositions suitable for oral administration include solid forms, such as pills, capsules, granules, tablets, and powders, and liquid forms, such as solutions, syrups, elixirs, and suspensions. Forms useful for topical administration include cream, ointment, gel, suspension, drops, emulsions, skin patches.

In addition to standard carriers, an oral pharmaceutical composition of the present invention may be supplemented with one or more excipients that are normally employed in oral formulations, such as surfactants, inhalants, solubilizers, stabilizers, emulsifiers, thickeners, coloring agents, sweetening agents, flavoring agents, and preservatives. Such excipients are well known to those skilled in the art.

According to the invention, the pharmaceutical composition may be administered to a subject through any route, such as oral administration or parenteral injection.

The term "effective amount" as used herein refers to a sufficient amount of a compound of the present invention to provide desired therapeutic effects, or the induction of a particular type of response. The effective amount required varies from subject to subject, depending on the disease state, physical conditions, age, sex, species and weight of the subject, etc. However, an appropriate effective amount can be determined by one of ordinary skill in the art using only routine experimentation.

The present invention is further illustrated by the following examples, which are provided for the purpose of demonstration rather than limitation.

EXAMPLES

Example 1: Computational Docking Simulations

Computational docking simulations were carried out to predict the binding of EH202 analogs to EPO-EPO receptor (EPOR) complex. Among our designed over 200 chemical molecules docked into models of computation simulation system, thirty three chemical molecules are selected as positive allosteric modulators (EH202~EH234) by free energy of binding to EPO-EPOR complex. We found that each EH202 analogs binds preferentially to the EPO-bound EPOR complex (EPO/EPOR) rather than the EPO-free naïve EPOR (estimated free energy of binding for EH202 analogs were ranging from −6.92 to −10.03 kcal·mol$^{-1}$, compared to −6.30 kcal·mol$^{-1}$ for EPO-free naïve EPOR). See Table 2 below.

TABLE 2

Estimated free energy of binding for EH202 analogs

| Compound | Estimated free energy of binding to EPO-bound EPOR complex |
|---|---|
| EH202 | −10.03 kcal/mol |
| EH203 | −9.06 kcal/mol |
| EH204 | −8.96 kcal/mol |
| EH205 | −8.78 kcal/mol |
| EH206 | −8.24 kcal/mol |
| EH207 | −7.65 kcal/mol |
| EH208 | −9.91 kcal/mol |
| EH209 | −9.88 kcal/mol |
| EH210 | −9.73 kcal/mol |
| EH211 | −9.73 kcal/mol |
| EH212 | −9.64 kcal/mol |
| EH213 | −9.52 kcal/mol |
| EH214 | −9.45 kcal/mol |
| EH215 | −9.38 kcal/mol |
| EH216 | −9.34 kcal/mol |
| EH217 | −9.31 kcal/mol |
| EH218 | −9.29 kcal/mol |
| EH219 | −9.18 kcal/mol |
| EH220 | −8.97 kcal/mol |
| EH221 | −8.87 kcal/mol |
| EH222 | −8.64 kcal/mol |
| EH223 | −8.54 kcal/mol |
| EH224 | −8.51 kcal/mol |
| EH225 | −8.04 kcal/mol |
| EH226 | −7.92 kcal/mol |
| EH227 | −7.84 kcal/mol |
| EH228 | −7.69 kcal/mol |
| EH229 | −7.60 kcal/mol |
| EH230 | −7.57 kcal/mol |
| EH231 | −7.52 kcal/mol |
| EH232 | −7.31 kcal/mol |
| EH233 | −7.18 kcal/mol |
| EH234 | −6.92 kcal/mol |

Example 2: Synthesis of EH222

1. Synthesis of (2-bromo-4,6-dimethoxyhydroxy-phenoxy)-O-aceton-β-D-glycoside

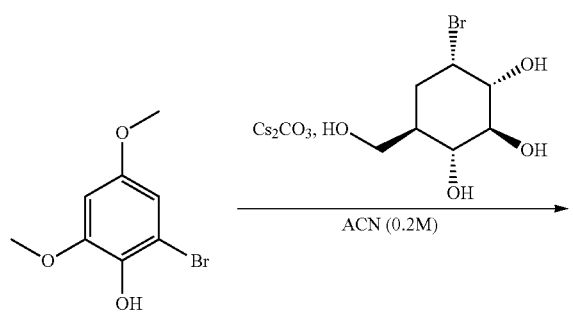

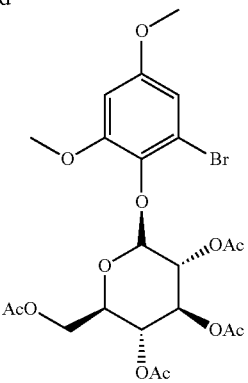

The mixtures of 2-bromo-4,6-dimethoxyphenol (5 mmol), cesium carbonate (5.5 mmole) and Acetonbromo-alpha-D-Glucose (15 mmole) in acetonitrile were stirred for 16 hours at room temperature under nitrogen. The inorganic precipitate was filtered off, and the filtrate was concentrated under reduce pressure. The residue was diluted with water and extracted with dichloromethane three times. The combined organic solution was dried over magnesium sulfate and evaporated by Rota Vapor. The residue purification was chromatographed on silica gel with EA/n-hexane as the eluent. The compound was white solid and the yield was 72%.

2. Synthesis of (2-hydroxy-3,5-dimethoxy-4′fluoro-stilbenzene)-2-O-aceton-β-D-glycoside

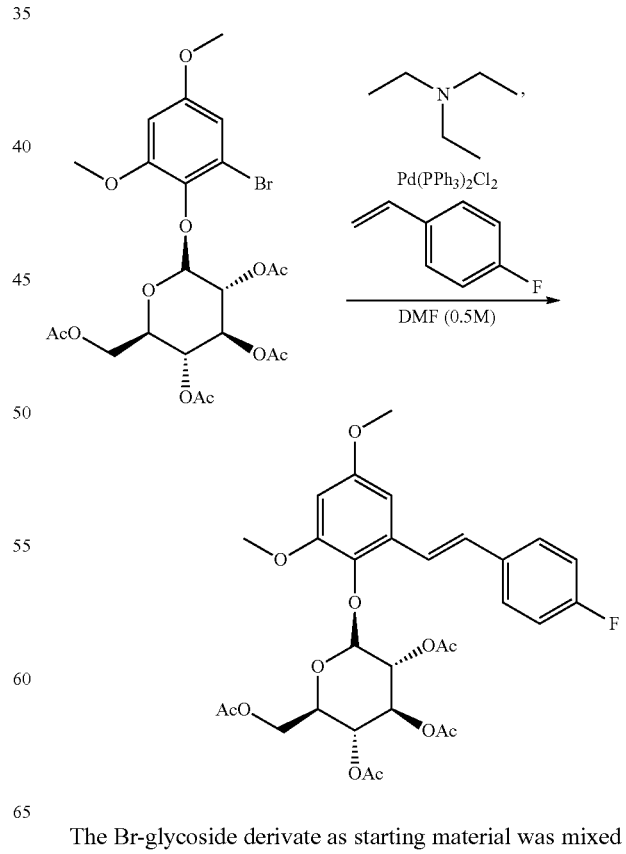

The Br-glycoside derivate as starting material was mixed with triethylamine (1.5 mmole) and 1-fluoro-4-vinylbenzene (1.5 mmole) in the presence of catalyst (Bis-triphenylphosphine) (5 mmole %) palladium dichloride to dissolve in dry/degas DMF at 110 degree over 20 hours. The reaction was monitored by TLC stain until the starting material was consumption. The solvent was removed by Rota Vapor and extracted by EA with water. The organic layer was dry magnesium sulfate. Then, the suspension was filtered and concentrated in vacuum. The residue purification was chromatographed on silica gel with EA/n-hexane as the eluent. The compound was white solid and the yield was 80%.

3. Synthesis of EH222

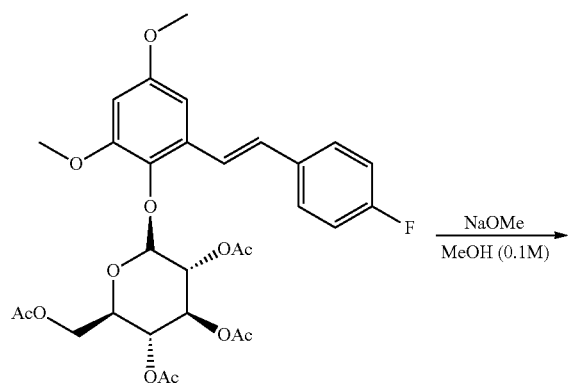

A solution of (2-hydroxy-3,5-dimethoxy-4'fluoro-stilbenzene)-2-O-aceton-β-D-glycoside in anhydrous methanol was treated with methanolic sodium methoxide for 6 hours. The reaction was monitored by TLC stain until the starting material was consumption. The mixture was neutralized with Amberlite IR-120(H+) and the residue purification was through short column with methanol as the eluent. The compound was white solid and the yield was 95%.

$^1$H NMR (400 MHz, CDCl$_3$, 25° C.): δ7.78 (d, $^3J_{H-H}$=16.5 Hz, 1H, CH), 7.63 (m, 2H, Ar—H), 7.11 (d, $^3J_{H-H}$=17.2 Hz, 1H, CH), 7.08 (m, 2H, Ar—H)), 6.84 (s, 1H, Ar—H), 6.56 (s, 1H, Ar—H), 4.74 (dd, $^3J_{H-H}$=7.6 Hz, $^4J_{H-H}$=2.28H, 1H, Glycoside), 4.30 (s, 6H, —OCH$_3$), 3.78 (m, 1H, Glycoside), 3.69 (m, 1H, Glycoside), 3.58 (m, 1H, Glycoside), 3.47 (m, 2H, Glycoside), 3.20 (m, 1H, Glycoside); LRMS(ESI$^+$): calculated for [M+H]$^+$: 459.15; Found: 459.2.

Example 3: Synthesis of EH232

1. Synthesis of (2-hydroxy-3,5,4'-trimethoxystilbenzene)-2-O-aceton-β-D-glycoside The reagent was replacement for 4-vinylanisole and followed the procedure as describe in Example 2. The product yield was 71%.

2. Synthesis of EH232

The procedure as describe in Example 2 was followed. The product yield was 98%.

$^1$H NMR (400 MHz, CDCl$_3$, 25° C.): δ7.55 (d, $^3J_{H-H}$=16.4 Hz, 1H, CH), 7.42 (d, $^3J_{H-H}$=8.8 Hz, 2H, Ar—H), 6.85 (d, $^3J_{H-H}$=16.0 Hz, 1H, CH), 6.84 (d, $^3J_{H-H}$=8.8 Hz, 2H, Ar—H), 6.65 (d, $^4J_{H-H}$=2.8 Hz, 1H, Ar—H), 6.29 (d, $^4J_{H-H}$=2.8 Hz, 1H, Ar—H), 4.50 (d, $^3J_{H-H}$=8.8 Hz, 1H, Glycoside), 4.30 (br, 4H, Glycoside-OH), 3.79 (s, 3H, —OCH$_3$), 3.76-3.61 (m, 7H, Glycoside), 3.72 (s, 6H, —OCH$_3$); LRMS(ESI$^+$): calculated for [M+H]$^+$: 471.17; Found: 471.2.

Example 4: Effects of the Compounds on the Formation of Hemoglobin in Bone Marrow Cells C57BL/6JNarl mice, 8-10 weeks of age, were purchased from National Laboratory Animal Center (NLAC, Taiwan) and used. Acute hemolytic anemia was induced by a single intraperitoneal (i.p.) injection phenylhydrazine hydrochloride (Sigma-Aldrich) at a dose of 100 mg/kg in phosphate buffered saline (PBS). Bone marrow cells from mice were isolated and cultured as reported earlier with minor modification 6 days after injection (Worthington et al., 1985 and Rosenthal et al., 1987). Cells were adjusted to about 6×10$^5$ cells/ml in MEM alpha medium (α-MEM, Gibco) containing 1% (v/v) bovine serum albumin (BSA, Sigma-Aldrich), 7.5 μM 2-mercaptoethanol (Sigma-Aldrich), 1.4 mM L-glutamine (Sigma-Aldrich), 10 μM ferric chloride (FeCl3, Sigma-Aldrich) and 50 mU/ml EPO (RecormonEpoetin, Roche), plated at approximately 1.5×10$^5$ cells/well on 96-well plates (Costar) and then cultured at 37° C. in a humidified incubator of 5% CO$_2$-95% air. Cells were treated with different concentrations of EH202~EH207, EH222 and EH232 (0, 0.1, 1, 10, and optionally, 100 μg/ml) the next day, and the relative level of hemoglobin were determined by DAF-based hemoglobin colorimetry assay (Kaihoand Mizuno, 1985 and Worthington et al., 1985) with minor modification 4 days later. In brief, cells were washed with PBS, lysed in 50 μl/well of 0.01% (v/v) Nonidet™ P 40 (NP-40, Sigma-Aldrich) and added with 100 μl/well of 100 μg/ml 4,5-diaminofluorescein (DAF, Sigma-Aldrich) as well as 6 μl/well of 30% hydrogen peroxide (Sigma-Aldrich). After incubation for 5-10 minutes, the absorbance at 620 nm was measured by a Victor 2 1420 Multilable Counter (Wallac, PerkinElmer). Results were expressed as relative index±S.E. (n=6) and statistical significance was evaluated by Student's t test (*P<0.05, P<0.01, *P<0.001 versus control group (0 μg/ml)). The results shows that the compounds significantly promote the formation of hemoglobin at the concentration of 0.1~100 μg/ml (FIGS. 1A-1G).

Example 5: EH202 Ameliorates Anaemia and Renal Function in Cisplatin-Induced Nephropathy 1. Materials and Methods Forty six-to-seven-week-old C57Bl/6J male mice were i.p. injected with three doses of cisplatin (Sigma-Aldrich), following the scheme of 7, 6, and 6 mg·kg-1 body weight, at 4 to 5 day intervals, and the normal group (n=4) was injected with saline (FIG. 1 scheme). On day 12, the collected serum samples were assayed for the urea nitrogen content (BUN). Mice with BUN values greater than 80 mg·dL-1 were chosen for the experiment. An average seventy percent of injected mice were successful induced renal dysfunction, and the ineffective mice were excluded from the EH202 treating experiments. The mice were subsequently divided randomly into 4 cohorts comprising the control (Ctrl, n=6) and three EH202-treated groups (n=5 to 6 for each group) for an additional 2 weeks. Blood samples from all the mice were collected every 5 days. The RBC numbers were determined from the complete blood cell count using a Sysmex Kx-21 haematology analyser (Sysmex America), and the serum BUN and creatinine levels were determined using a commercial kit (Randox Laboratories Ltd. United Kingdom). All results are expressed as the mean±SEM. The statistical analysis was performed using Student's t-test. One-way ANOVA was used to examine the differences across the animal experimental groups. The posthoc differences between the means of the experimental groups were determined via Tukey's test. P<0.05 was considered significant.

2. Results

Figure 2A:
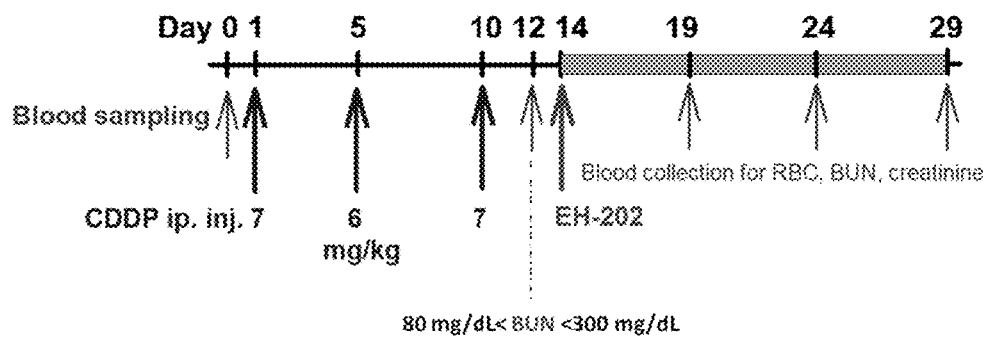
FIG. 2A is a schematic diagram showing the protocol for investigating the therapeutic effects of EH202 after cisplatin (CDDP)-induced nephropathic mice.
Figure 2B:
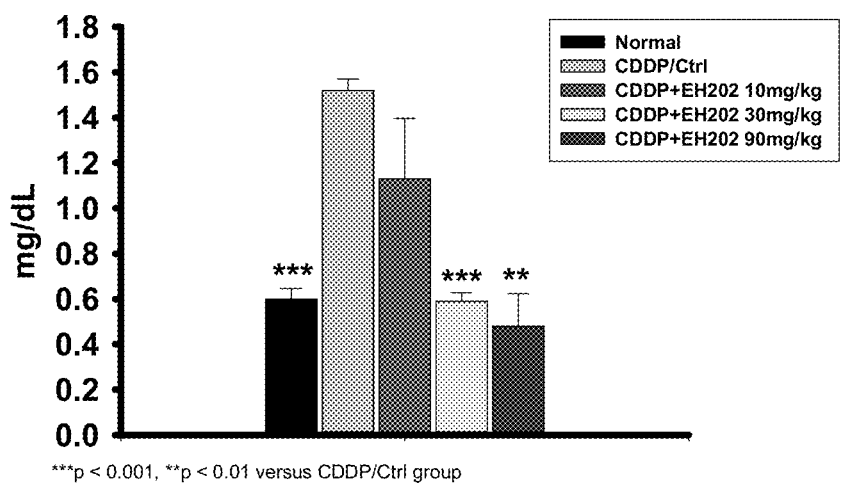
FIG. 2B shows that EH202 accelerates the recovery from renal dysfunction in cisplatin-induced nephropathy in mice. The functional recovery of the kidneys of mice treated with EH202 on day 24 was measured by creatinine level in the peripheral blood. The values are presented as the means±SEM (n=3-6 animals each group). *p<0.001, p<0.01 versus control group.
Figure 2C:
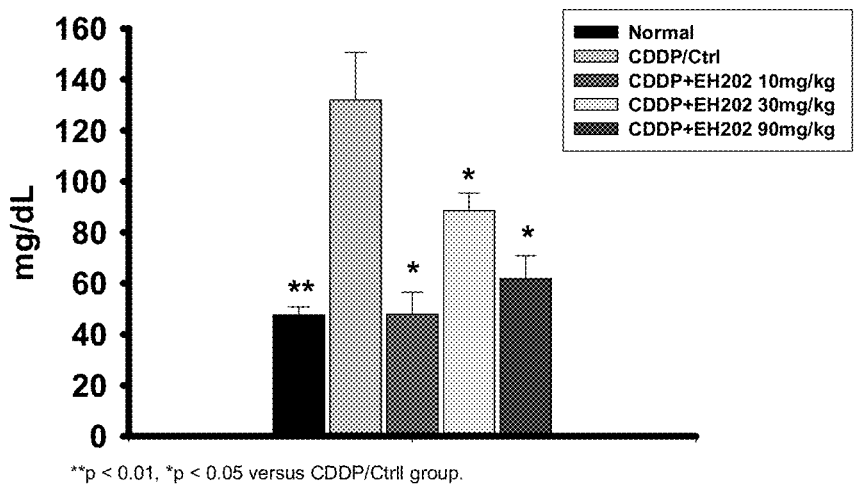
FIG. 2C shows that EH202 accelerates the recovery from renal dysfunction in cisplatin-induced nephropathy in mice. The functional recovery of the kidneys of mice treated with EH202 on day 29 was measured by BUN level in the peripheral blood. The values are presented as the means±SEM (n=3-6 animals each group). **p<0.01, *p<0.05 versus control group.
Figure 2D:
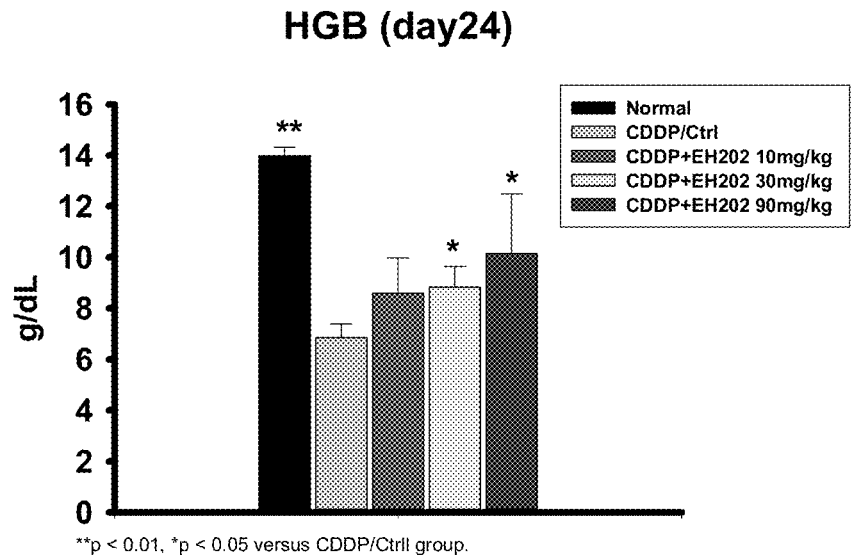
FIG. 2D shows that EH202 accelerates the recovery from anemia in cisplatin-induced nephropathy in mice. The functional recovery of the RBC of mice treated with EH202 on day 24 was measured by hemoglobin (HGB) level in the peripheral blood. The values are presented as the means±SEM (n=3-6 animals each group). **p<0.01, *p<0.05 versus control group.
Figure 2E:
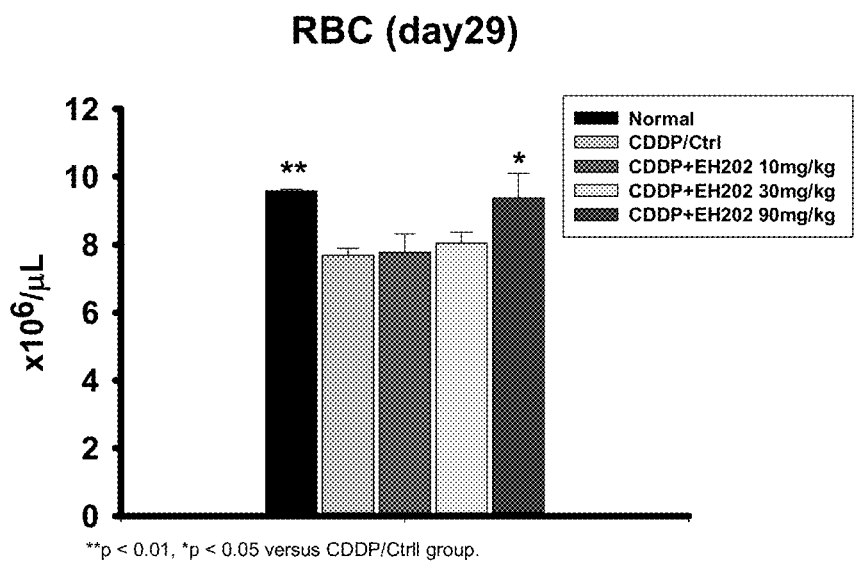
FIG. 2E shows that EH202 accelerates the recovery from anemia in cisplatin-induced nephropathy in mice. The functional recovery of the RBC of mice treated with EH202 on day 29 was measured by RBC numbers in the peripheral blood. The values are presented as the means±SEM (n=3-6 animals each group). **p<0.01, *p<0.05 versus control group.

Because acute kidney injury may result from renal ischemia caused by the use of nephrotoxic agents and to examine the effect of EH202-induced EPO production on the anaemia with renal insufficiency, we adopted an established cisplatin-induced nephropathy mouse model (FIG. 2A). We observed significant impaired renal function from day 12 and anaemia from day 19 after the first injection of cisplatin. Notably, the administration of 30 and 90 mg·kg-1 of EH202 for 10 days (on day 24, FIG. 2B) led to an almost complete recovery of renal dysfunction. Moreover, the BUN levels of the EH202 10, 30 and 90 mg·kg-1 treatment groups were also significantly recovered (FIG. 2C). Furthermore, the administration of 30 and 90 mg·kg-1 of EH202 (FIGS. 2D and 2E) led to an increasing recovery of anaemia. Collectively, these findings suggest that EH202 improved the recovery from cisplatin-induced anaemia and renal dysfunction.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A compound, which is a positive allosteric modulator for erythropoietin and erythropoietin receptor and has a formula selected from the group consisting of:

EH202
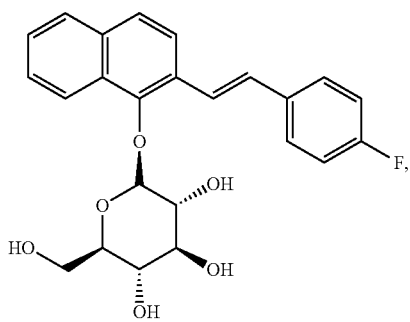

-continued

EH203
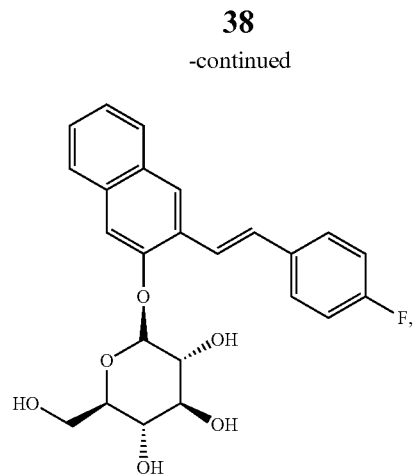

EH204
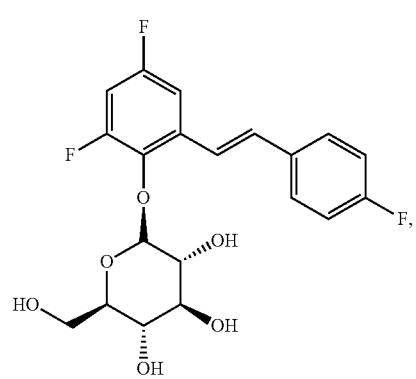

EH205
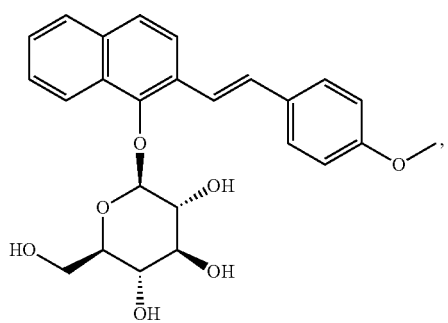

EH206
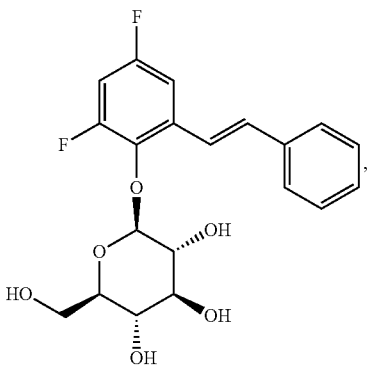

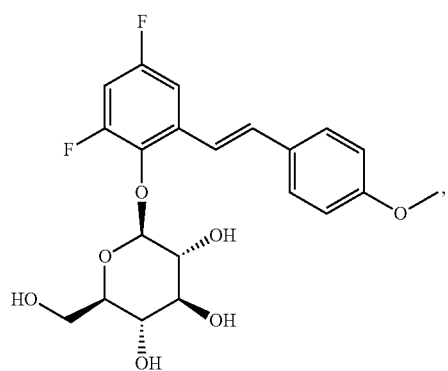
EH207
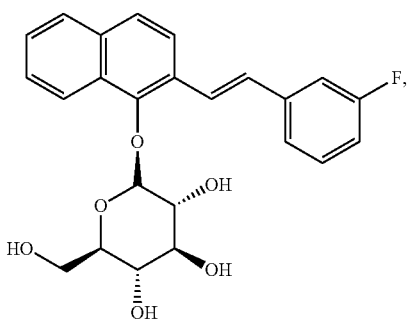
EH211
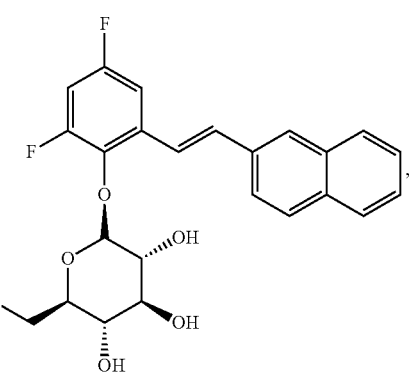
EH212
EH208
EH209
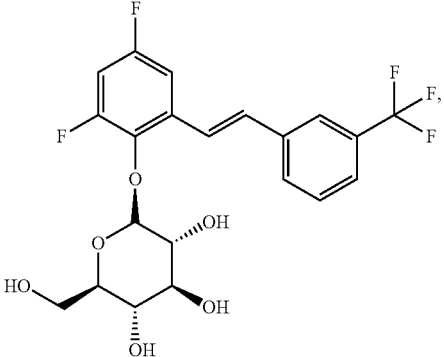
EH213
EH210
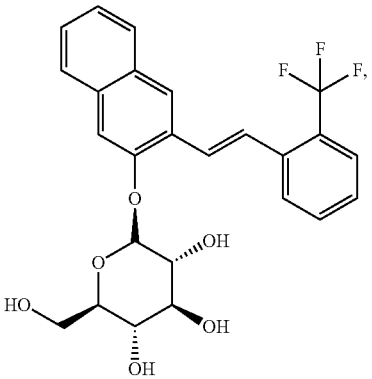
EH214

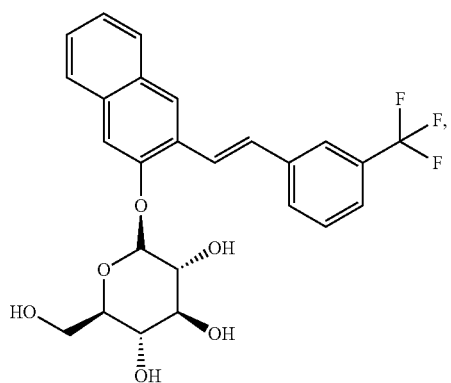 EH215
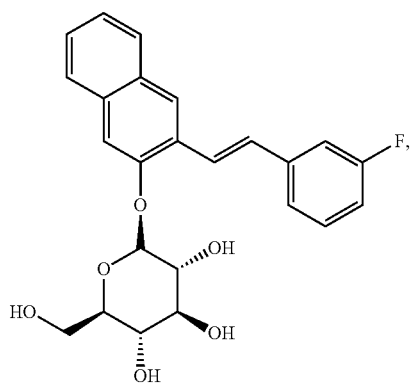 EH219
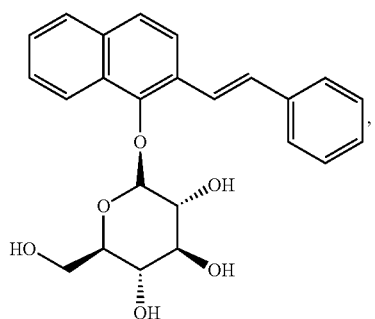 EH216
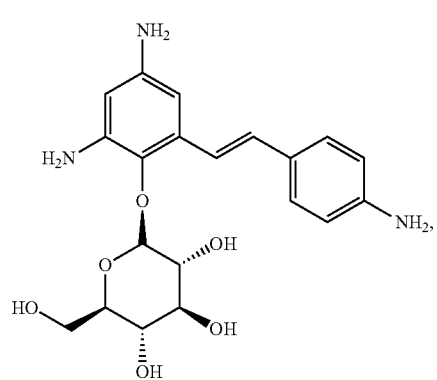 EH220
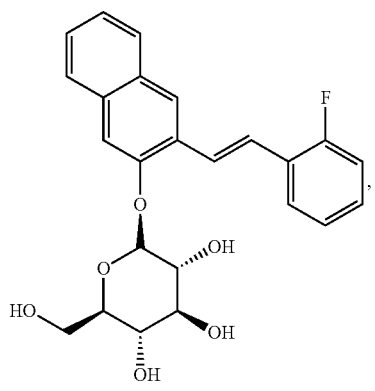 EH217
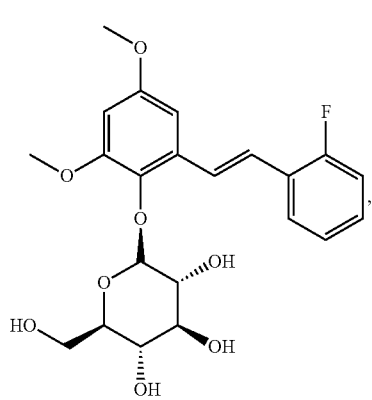 EH221
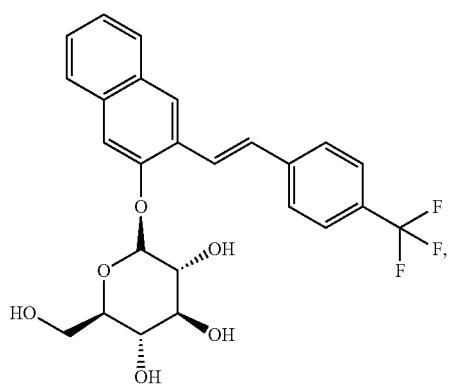 EH218
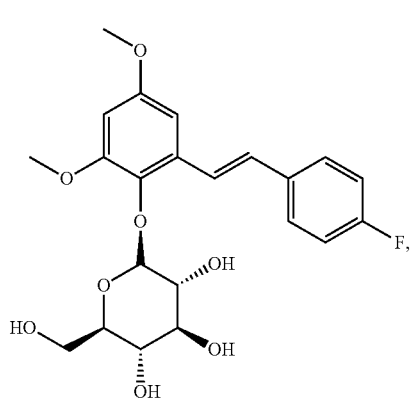 EH222

EH223
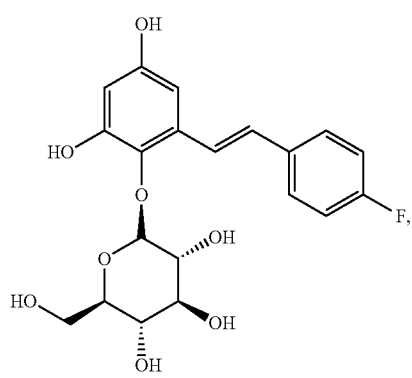
EH227
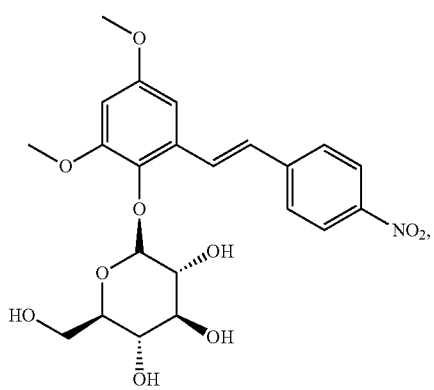
EH224
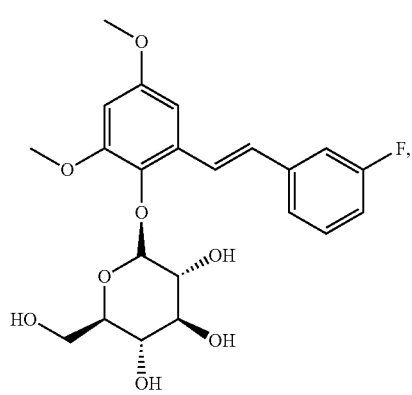
EH228
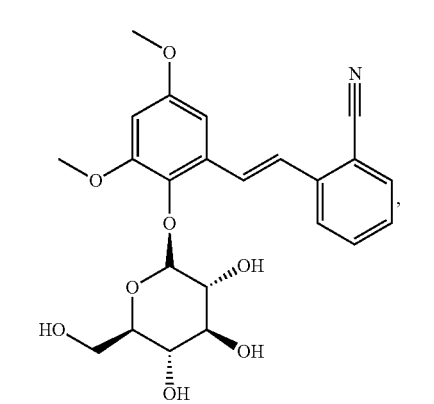
EH225
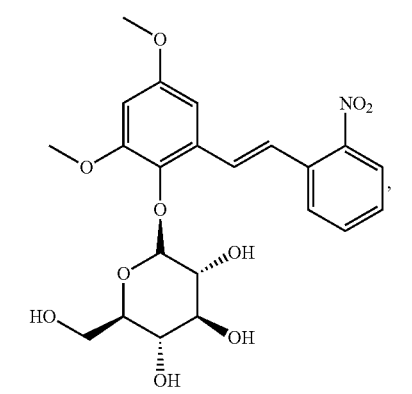
EH229
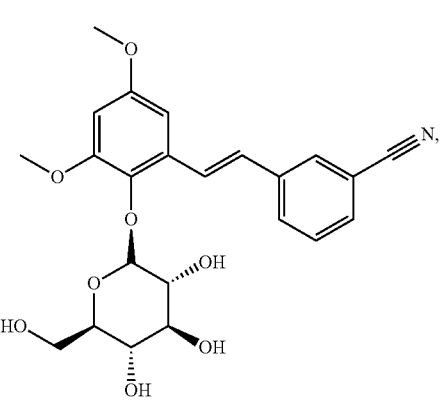
EH226
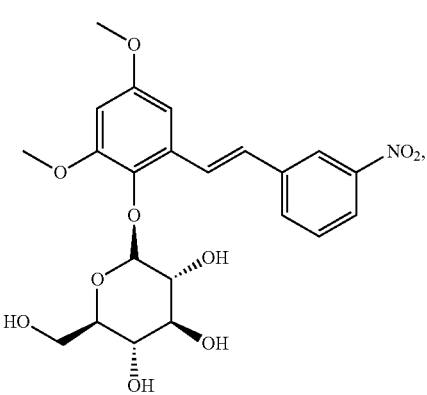
EH230
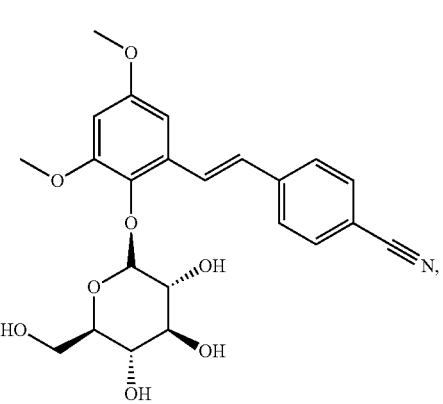

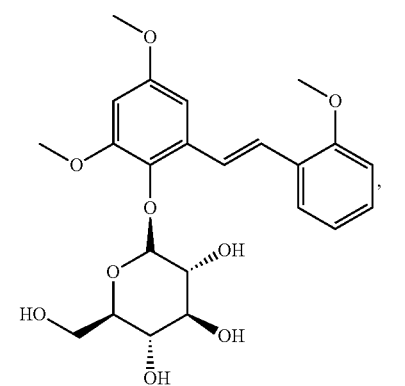
EH231
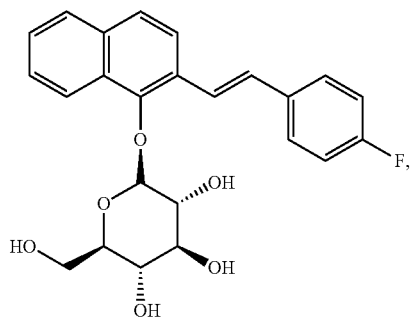
EH202
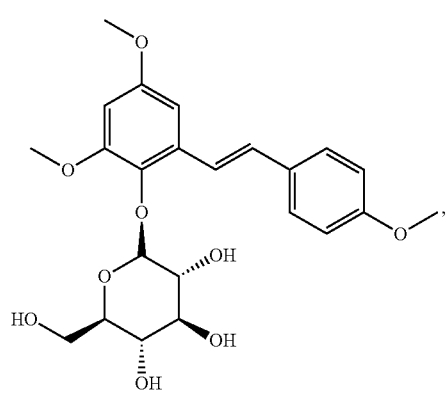
EH232
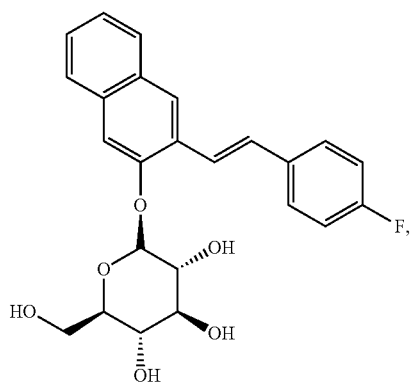
EH203
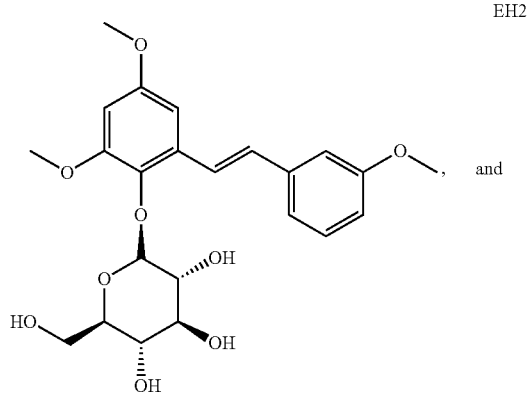
EH233, and
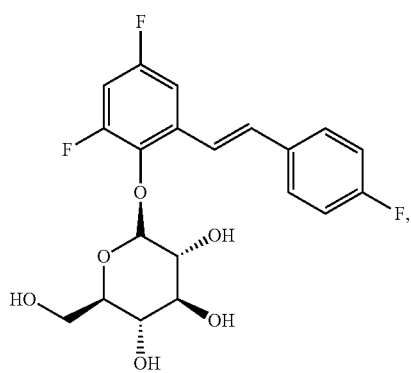
EH204
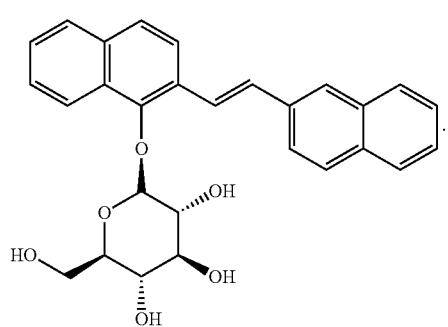
EH234
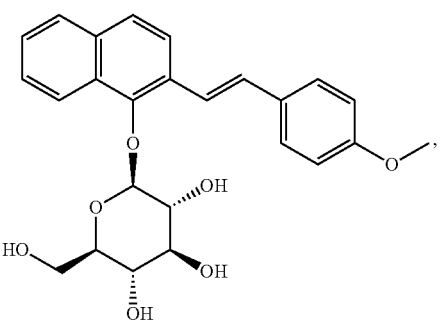
EH205
2. The compounds of claim 1, having a formula selected from the group consisting of:

EH206

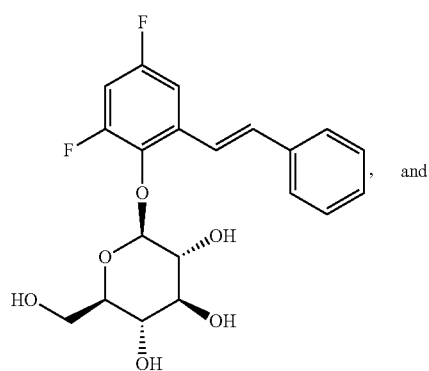

, and

EH207

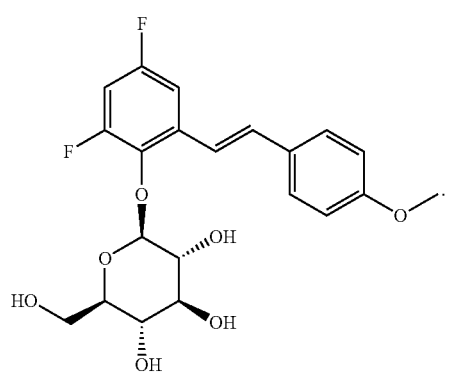

3. The compound of claim 1 for use in treating an erythropoietin deficiency disease by acting as a positive allosteric modulator for erythropoietin and erythropoietin receptor.

4. The compound of claim 2 for use in treating an erythropoietin deficiency disease by acting as a positive allosteric modulator for erythropoietin and erythropoietin receptor.

5. A pharmaceutical composition comprising a compound according to claim 1, and a pharmaceutically acceptable carrier.

6. The pharmaceutical composition of claim 5, wherein the compound has a formula selected from the group consisting of:

EH202

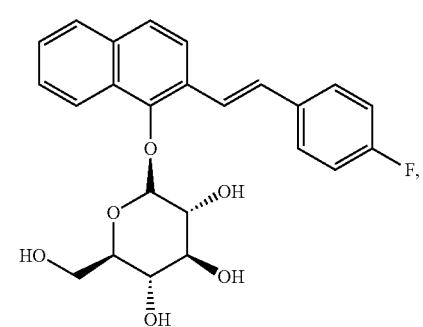

EH203

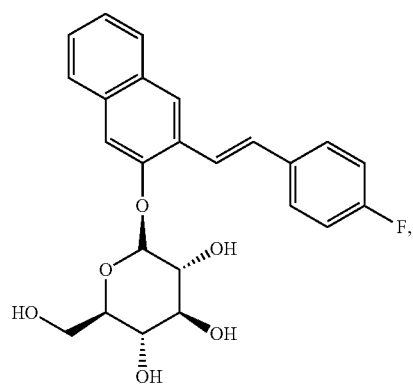

EH204

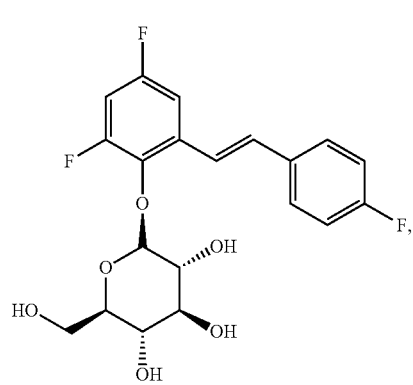

EH205

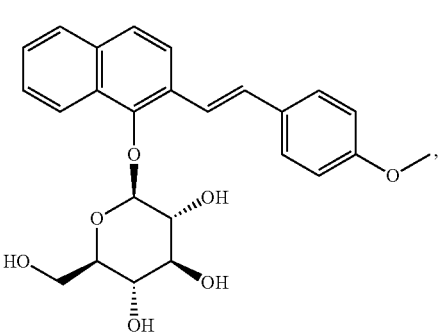

EH206

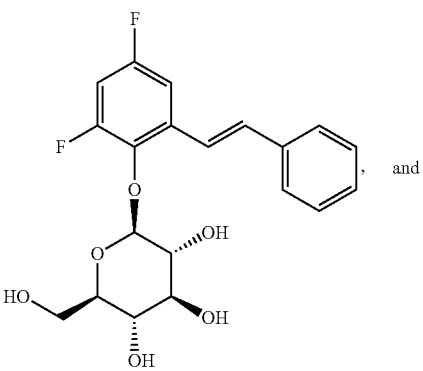

, and

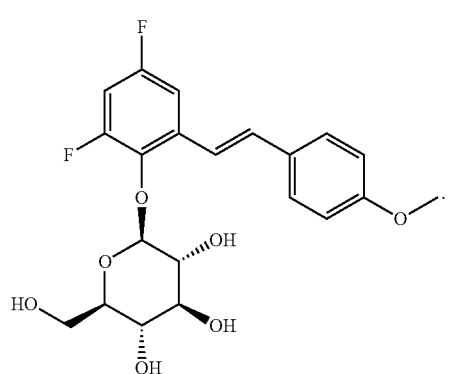

EH207

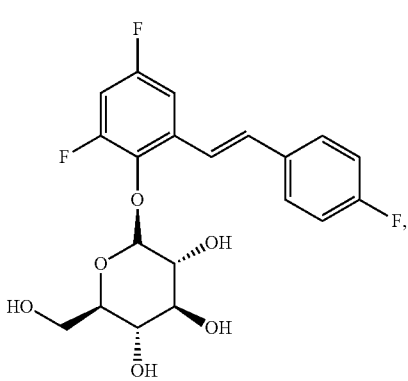

EH204

7. The pharmaceutical composition of claim 5 for treating an erythropoietin deficiency disease.

8. The pharmaceutical composition of claim 7, wherein the erythropoietin deficiency disease is selected from the group consisting of anemia, a chronic kidney disease, chronic heart failure, a neurodegenerative disease, age-related macular degeneration, a chronic obstructive pulmonary disease, an anemic cancer in a patient undergoing chemotherapy, dry eye, and aging related insomnia.

9. The pharmaceutical composition of claim 8, wherein the erythropoietin deficiency disease is anemia.

10. The pharmaceutical composition of claim 9, wherein the erythropoietin deficiency disease is anemia associated with a kidney disease.

11. A method for treating an erythropoietin deficiency disease comprising administering to a subject in need thereof an effective amount of a compound according to claim 1.

12. The method of claim 11, wherein the compound has a formula selected from the group consisting of:

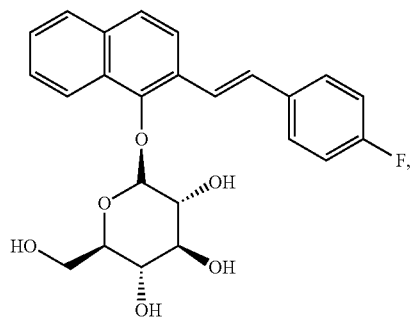

EH202

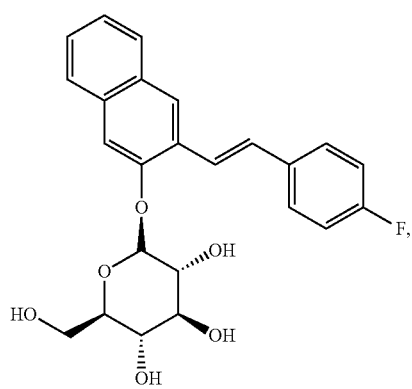

EH203

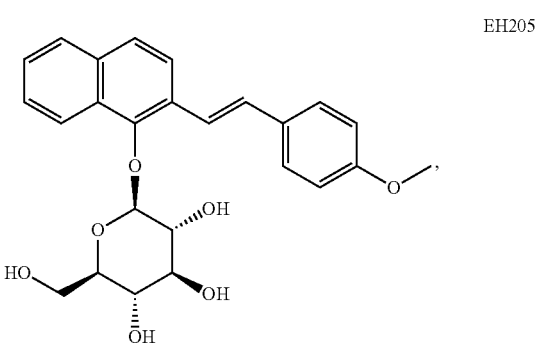

EH205

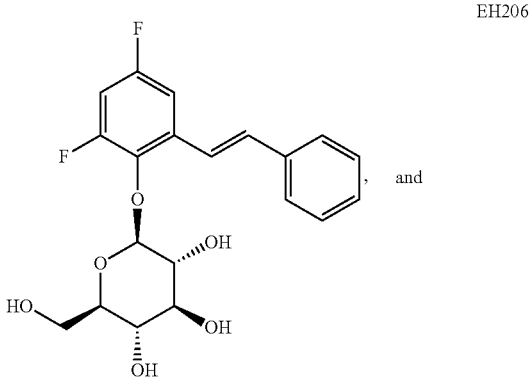

EH206

, and

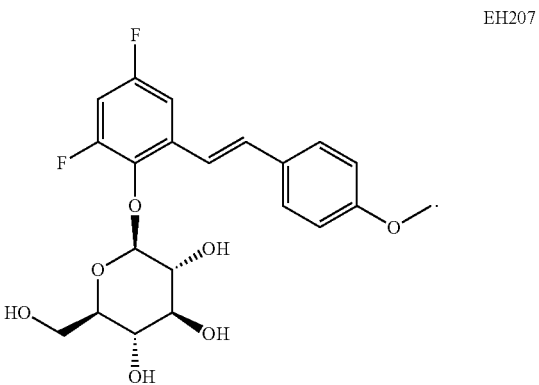

EH207

13. The method of claim 11, wherein the erythropoietin deficiency disease is selected from the group consisting of anemia, a chronic kidney disease, chronic heart failure, a neurodegenerative disease, age-related macular degeneration, a chronic obstructive pulmonary disease, an anemic cancer in a patient undergoing chemotherapy, dry eye, and aging related insomnia.

14. The method of claim 13, wherein the erythropoietin deficiency disease is anemia.

15. The method of claim 14, wherein the erythropoietin deficiency disease is anemia associated with a kidney disease.

* * * * *